United States Patent

Bronstein et al.

[11] Patent Number: 5,994,073
[45] Date of Patent: *Nov. 30, 1999

[54] ENHANCEMENT OF CHEMILUMINESCENT ASSAYS

[75] Inventors: Irena Y. Bronstein, Newton; Brooks Edwards, Cambridge; John C. Voyta, North Reading, all of Mass.

[73] Assignee: Tropix, Inc., Bedford, Mass.

[*] Notice: This patent is subject to a terminal disclaimer.

[21] Appl. No.: 08/850,009

[22] Filed: May 1, 1997

Related U.S. Application Data

[63] Continuation of application No. 08/588,260, Jan. 18, 1996, Pat. No. 5,654,154, and a continuation-in-part of application No. 07/806,928, Dec. 12, 1991, Pat. No. 5,330,900, which is a division of application No. 07/574,786, Aug. 30, 1990, Pat. No. 5,112,960, said application No. 08/588,260, is a continuation of application No. 08/031,471, Mar. 15, 1993, Pat. No. 5,547,836, which is a continuation-in-part of application No. 07/959,531, Oct. 13, 1992, Pat. No. 5,639,907.

[51] Int. Cl.$^6$ .................................................... C12Q 1/68
[52] U.S. Cl. .......................... 435/6; 436/501; 935/77; 935/78
[58] Field of Search .................. 435/6, 810; 436/501; 935/77, 78

[56] References Cited

U.S. PATENT DOCUMENTS 4,959,182  9/1990  Schaap ................................. 252/700

FOREIGN PATENT DOCUMENTS 9705209  2/1997  WIPO .

Primary Examiner—Ardin H. Marschel
Attorney, Agent, or Firm—Long Aldridge & Norman LLP; Steven B. Kelber

[57] ABSTRACT

Chemiluminescent bioassays for the presence or concentration of an analyte in a sample use 1,2-dioxetanes as substrates for the enzyme of an enzyme complex that bind to the analyte. The chemiluminescence obtained from the decomposition of the dioxetane triggered by the enzyme through the formation of the corresponding 1,2-dioxetane oxyanion of the enzyme complex is enhanced by the addition of TBQ as an enhancement agent. Other polymeric quaternary onium salts can be used as enhancement agents in conjunction with enhancement additives which improve the ability of the enhancement agent to form hydrophobic regions in the aqueous sample, in which regions the 1,2-dioxetane oxyanion and its chemiluminescent decomposition products can be sequestered. A kit for performing such assays is also provided.

17 Claims, 4 Drawing Sheets

5,994,073

ENHANCEMENT OF CHEMILUMINESCENT ASSAYS

BACKGROUND OF THE INVENTION

This is a Continuation of application Ser. No. 08/588,260 filed on Jan. 18, 1996, now U.S. Pat. No. 5,654,154; which is a Continuation application of Ser. No. 08/031,471 filed on Mar. 15, 1993, now U.S. Pat. No. 5,547,836 which application Ser. No. 08/031,471; now U.S. Pat. No. 5,547,836 is in turn a continuation-in-part of U.S. patent application Ser. No. 07/806,928, filed Dec. 12, 1991 now U.S. application No. 5,330,900 itself a divisional application of U.S. patent application Ser. No. 07/574,786, filed Aug. 30, 1990 issued as U.S. Pat. No. 5,112,960. The entire disclosure of U.S. Pat. No. 5,112,960 is incorporated herein by reference. Application Ser. No. 08/031,471; now U.S. Pat. No. 5,547,836 is also in turn a continuation-in-part application of U.S. patent application Ser. No. 07/959,531, filed Oct. 13, 1992, now U.S. Pat. No. 5,639,907, the entire disclosure of which is incorporated hereby reference.

FIELD OF THE INVENTION

This invention pertains to the enhancement of chemiluminescent assays for analytes in a sample, generally a biological sample, based on the use of 1,2-dioxetanes as chemiluminescent substrates for enzyme-labeled targets or probes. The chemiluminescence of the dioxetane reporter molecule can be enhanced by the addition of a water-soluble quaternary polymer. Further enhancement can be achieved by additionally including in the sample an additive which improves the ability of the water-soluble quaternary polymer to sequester the dioxetane within hydrophobic regions formed by the water-soluble polymer thereby suppressing or avoiding water-induced light quenching reactions.

BACKGROUND OF THE PRIOR ART

Chemiluminescent assays for the detection of the presence or concentration of an analyte in a sample, generally a biological sample, have received increasing attention in recent years as a fast, sensitive and easily read method of conducting bioassays. In such assays, a chemiluminescent compound is used as a reporter molecule, the reporter molecule chemiluminescing in response to the presence or the absence of the suspected analyte.

A wide variety of chemiluminescent compounds have been identified for use as reporter molecules. One class of compounds receiving particular attention is the 1,2-dioxetanes. 1,2-dioxetanes can be stabilized by the addition of a stabilizing group to at least one of the carbon molecules of the dioxetane ring. An exemplary stabilizing group is spiro-bound adamantane. Such dioxetanes can be further substituted at the other carbon position with an aryl moiety, preferably phenyl or naphthyl, the aryl moiety being substituted by an oxygen which is in turn bound to an enzyme-labile group. When contacted by an enzyme capable of cleaving the labile group, the oxyanion of the dioxetane is formed, leading to decomposition of the dioxetane and spontaneous chemiluminescence. A wide variety of such dioxetanes are disclosed in U.S. Pat. No. 5,112,960. That patent focuses on dioxetanes which bear a substituent on the adamantyl-stabilizing group, such as halo substituents, alkyl groups, alkoxy groups and the like. Such dioxetanes represent an advance over earlier-recognized dioxetanes, such as 3-(4-methoxyspiro[1,2-dioxetane-3,2'-tricyclo]-3.3.1.1$^{3,7}$] decan]-4-yl)phenyl phosphate, and in particular, the disodium salt thereof, generally identified as AMPPD. The chlorine-substituted counterpart, which converts the stabilizing adamantyl group from a passive group which allows the decomposition reaction to go forward to an active group which gives rise to enhanced chemiluminescence signal due to faster decomposition of the dioxetane anion, greater signal-to-noise values and better sensitivity, is referred to as CSPD. Other dioxetanes, such as the phenyloxy-β-D-galactopyranoside (AMPGD) are also well known, and can be used as reporter molecules. These dioxetanes, and their preparation, do not constitute an aspect of the invention herein, per se.

Assays employing these dioxetanes can include conventional assays, such as Southern, Northern and Western blot assays, DNA sequencing, ELISA, as well as other liquid phase and mixed phase assays. In general, the assay consists of binding the target, if present in the sample, with a complex bearing an enzyme capable of cleaving the enzyme labile group of the dioxetane. In DNA assays, the target is bound by a DNA probe with an enzyme covalently linked thereto, the probe being admixed with the sample immobilized on a membrane, to permit hybridization. Thereafter, excess enzyme complex is removed, and dioxetane added to the hybridized sample. If hybridization has occurred, the dioxetane will be triggered by the bound enzyme, leading to decomposition of the dioxetane, and chemiluminescence. In liquid phase assays, the enzyme is frequently conjugated or complexed with an antibody responsive to the target analyte, unbound complex being removed, and the dioxetane added, chemiluminescence being produced by the decomposition of the dioxetane triggered by the amount of enzyme present. In cases where the enzyme itself is the target analyte, the dioxetane need only be added to the sample. Again, a wide variety of assay modalities has been developed, as disclosed in U.S. Pat. No. 5,112,960, as well as U.S. Pat. No. 4,978,614.

It has been well known that light-quenching reactions will occur if the dioxetane decomposition goes forward in a protic solvent, such as water. As the samples suspected of containing or lacking the analyte in question are generally biological samples, these assays generally take place in an aqueous environment. The light-quenching reactions therefor may substantially reduce the chemiluminescence actually observed from the decomposition of the dioxetane. In assays involving low-level detections of particular analytes, such as nucleic acids, viral antibodies and other proteins, particularly those prepared in solution or in solution-solid phase systems, the reduced chemiluminescence observed, coupled with unavoidable background signals, may reduce the sensitivity of the assay such that extremely low levels cannot be detected. One method of addressing this problem is the addition of water-soluble macromolecules, which may include both natural and synthetic molecules, as is disclosed in detail in U.S. Pat. No. 5,145,772. The disclosure of this patent is incorporated herein, by reference. To similar effect, U.S. Pat. No. 4,978,614 addresses the addition of various water-soluble "enhancement" agents to the sample, although the patent speaks to the problem of suppressing non-specific binding in solid state assays. In U.S. Pat. No. 5,112,960, preferred water-soluble polymeric quaternary ammonium salts such as poly(vinylbenzyltrimethylammonium chloride) (TMQ) poly(vinyl-benzyltributylammonium chloride) (TBQ) and poly(vinylbenzyl-dimethylbenzylammonium chloride) (BDMQ) are identified as water-soluble polymeric quaternary ammonium salts which enhance chemiluminescence by the suppression of non-specific binding.

Notwithstanding the advances in technology addressed by these assays, it remains a goal of the industry to provide chemiluminescent assays of greater sensitivity, to determine the presence, concentration or both of an analyte in a sample which is generally biological, and therefor, in an assay in an aqueous environment. 1,2-dioxetane compounds have already been developed which show excellent potential as reporter molecules for such chemiluminescent assays. To be used in extremely low-level detection, however, and/or to improve reliability to provide for machine readability, it is necessary to further improve the enhancement of the chemiluminescence of the 1,2-dioxetane molecules produced in aqueous preparations.

SUMMARY OF THE INVENTION

Applicants' invention addresses the above goals in two embodiments. As noted above, it has been previously recognized that the addition of water-soluble polymeric ammonium salts to the aqueous sample improves or enhances chemiluminescence of 1,2-dioxetanes. Applicants have discovered that this enhancement is achieved, at least in part, through the formation of hydrophobic regions in which the dioxetane oxyanion is sequestered. Decomposition in these hydrophobic regions enhances chemiluminescence, because water-based light quenching reactions are suppressed. Among the recognized water-soluble quaternary polymer salts employed, TBQ provides unexpectedly superior enhancement, through this hydrophobic region-forming mechanism.

The chemiluminescent enhancement achieved by the addition of water-soluble polymeric quaternary polymer salts can be further improved by the inclusion, in the aqueous sample, of an additive, which improves the ability of the quaternary polymeric salt to sequester the dioxetane oxyanion and the resulting excited state emitter reporting molecule in a hydrophobic region. Thus, the combination of the polymeric quaternary salt and the additive, together, produce an increase in enhancement far beyond that produced separately by the addition of the polymeric quaternary salt, or the additive, which, when a surfactant or water-soluble polymer itself, may enhance chemiluminescence to a limited degree. The synergistic combination of the polymeric quaternary salt and additives gives enhancement effects making low-level, reliable detection possible even in aqueous samples through the use of 1,2-dioxetanes. The polymeric quaternary salts, coupled with the additives, are sufficiently powerful enhancers to show dramatic 4 and 5-fold increases at levels below 0.005 percent down to 0.001 percent. Increased signal, and improved signal/noise ratios are achieved by the addition of further amounts of the polymeric quaternary salt, the additive, or both, in amounts up to as large as 50 percent or more. In general, levels for both polymeric quaternary salt and additive can be preferably within the range of 0.05–25 percent, more preferably from 0.1–15 percent by weight.

DETAILED DESCRIPTION OF THE INVENTION

Figure 1:
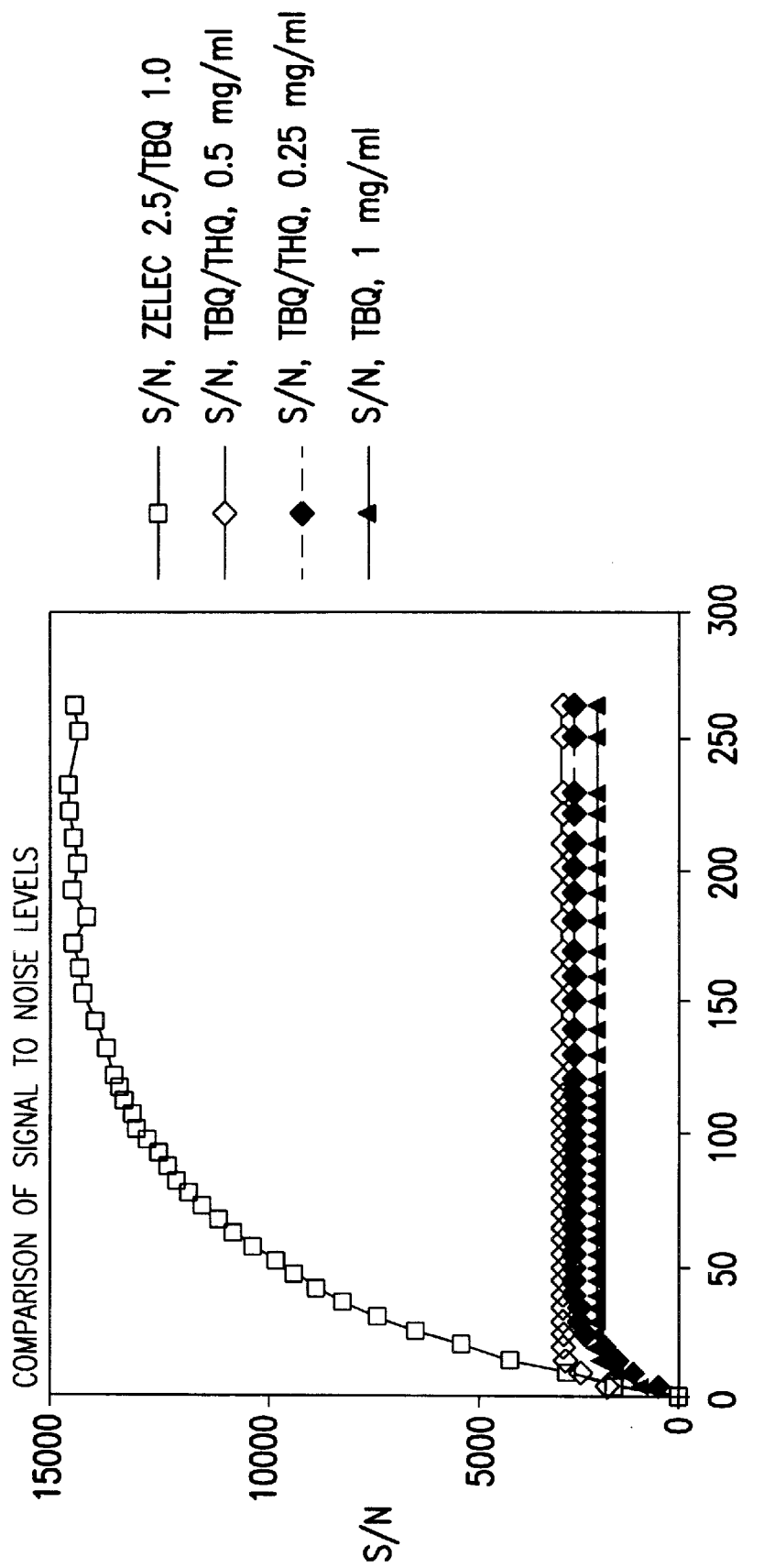
FIG. 1 shows a comparison of signal to noise levels for various enhancement additives and mixtures of enhancement additives.
Figure 2:
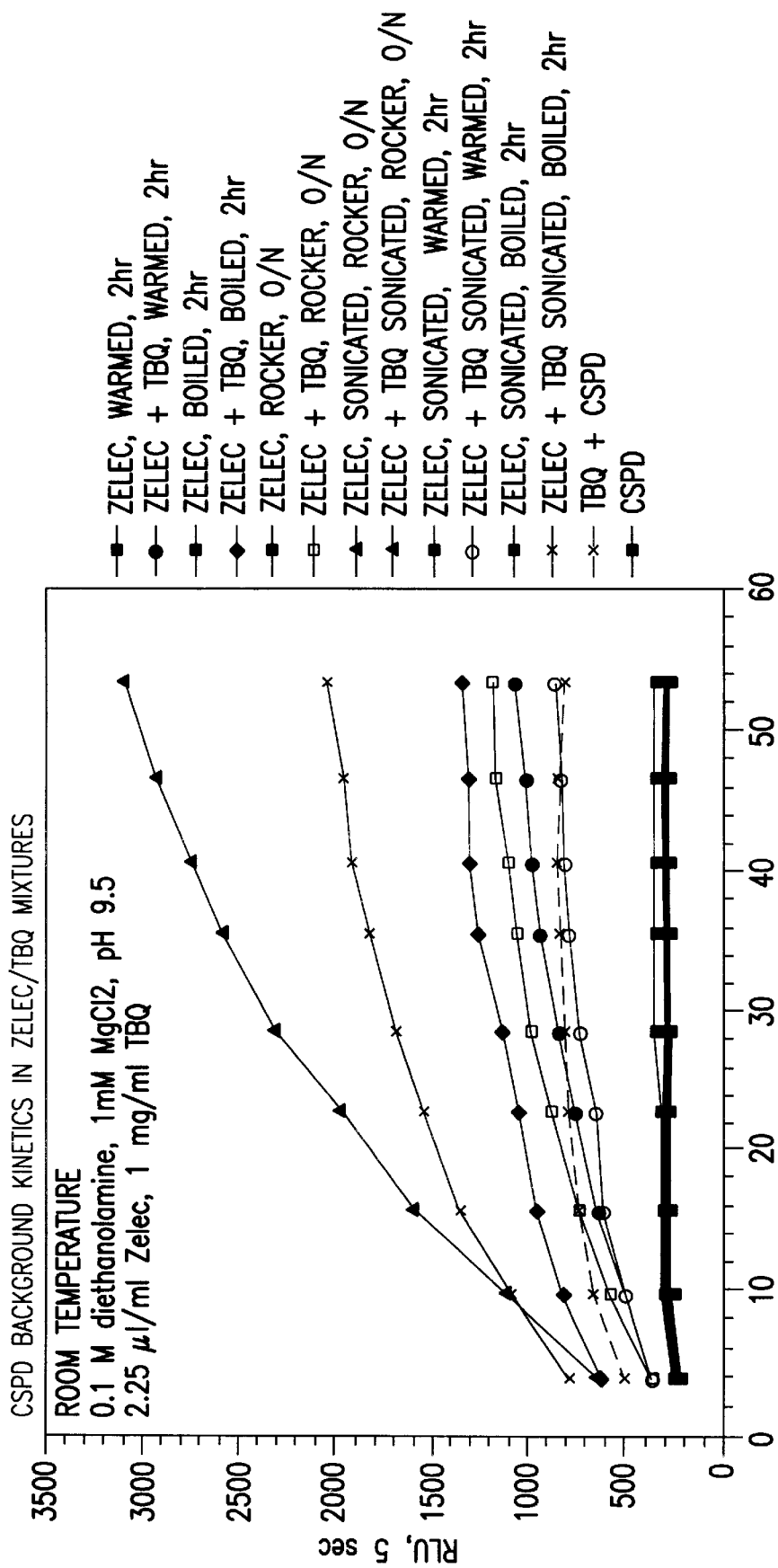
FIG. 2 shows the background kinetics of CSPD in combination with a mixture of Zelec and TBQ enhancement additives.
Figure 3:
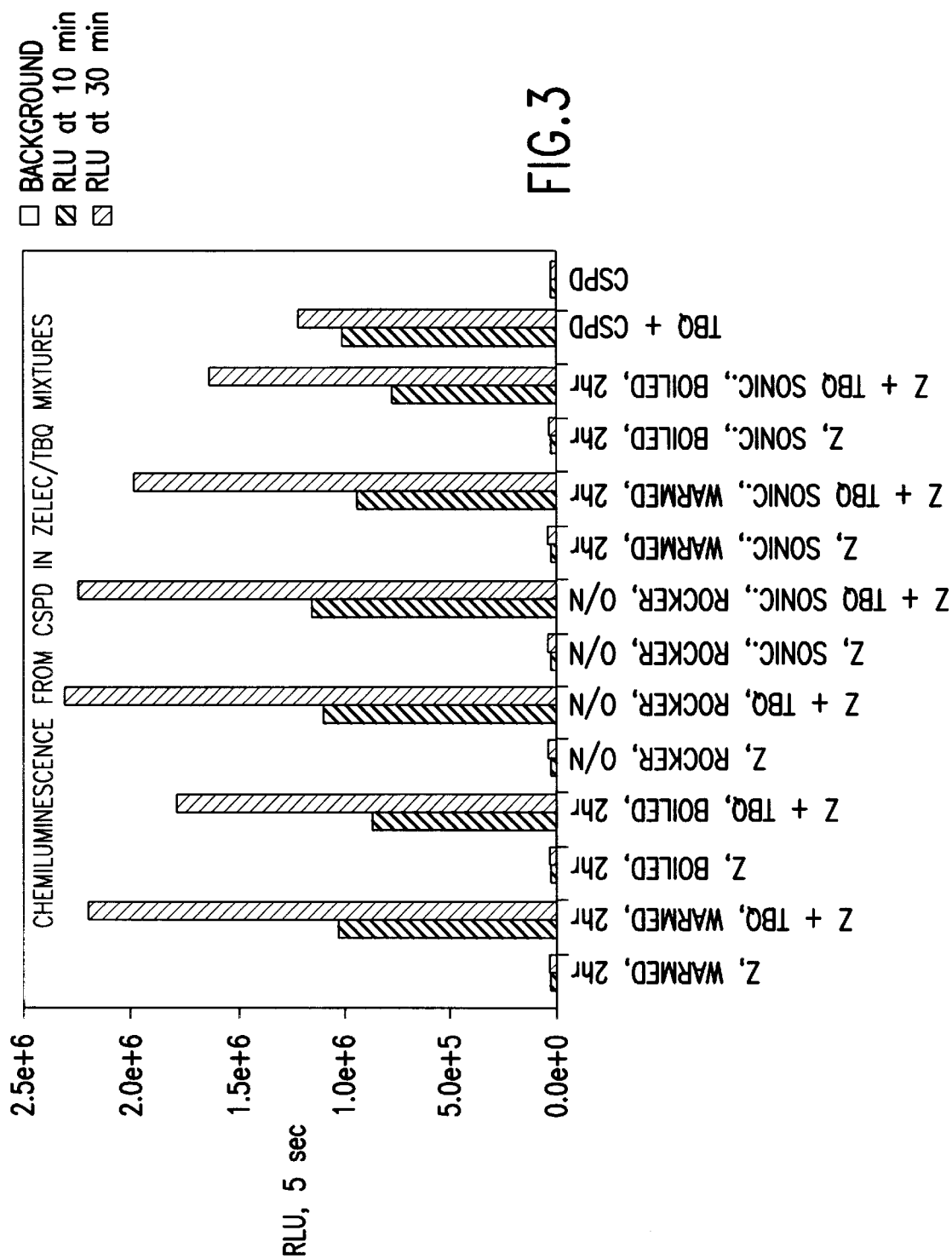
FIG. 3 shows the chemiluminescence produced using a combination of CSPD and a mixture of Zelec and TBQ as enhancement additives.
Figure 4:
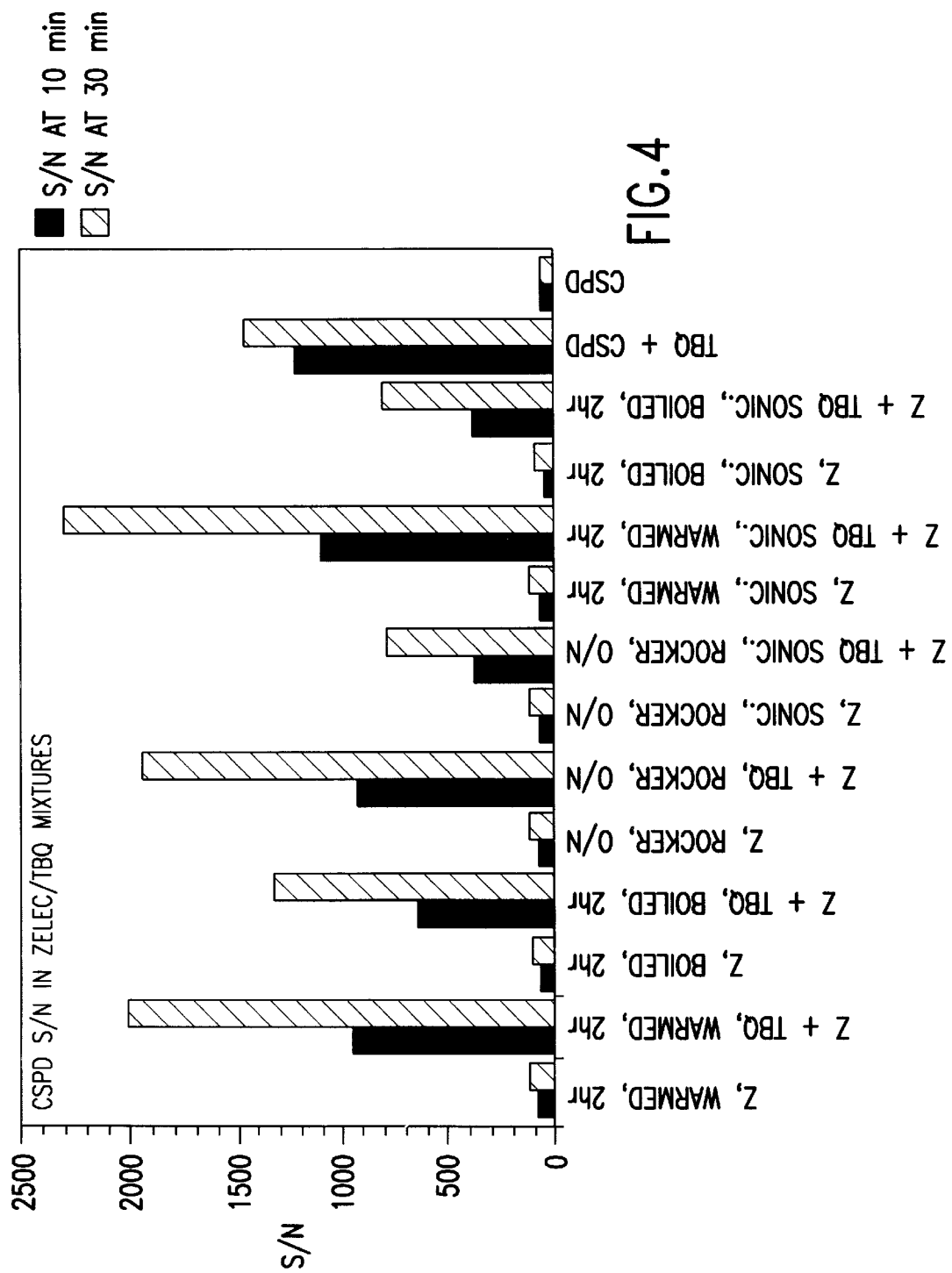
FIG. 4 shows the signal to noise ratio for CSPD in combination with a mixture of Zelec and TBQ as enhancement additives.

The assays and kits of this invention employ water-soluble chemiluminescent 1,2-dioxetanes. As noted above, these dioxetanes are well established in the art, and their identity and preparation does not constitute a novel aspect of this invention, per se. In general, any chemiluminescent dioxetane which exhibits sufficient stability in water to conduct the assay, and which may be caused to decompose and chemiluminesce by interaction with an enzyme, and cleavage, by the enzyme, of an enzyme labile group inducing the decomposition, can be used in connection with this invention. Typically, the 1,2-dioxetanes useful in this invention will have the general formula:

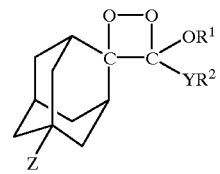

$R^1$ is $C_1$–$C_2$ alkyl or $C_{1-12}$ aryl or aralkyl;

Y is phenyl or naphthyl;

$R^2$ is meta-substituted or non-conjugated on Y with respect to the dioxetane, and is OX, wherein;

X is an enzyme cleavable group which, when cleaved, leaves the dioxetane phenoxy or naphthoxy anion;

Z=H, Cl, other halogens, or alkoxy groups.

Preferred dioxetanes include AMPPD, and in particular, its disodium salt, as well as CSPD and its disodium salt. Methods of preparing these dioxetanes are disclosed in the aforereferenced commonly-assigned patents, as well as, e.g., U.S. Pat. No. 4,962,162, assigned to Wayne State University. The preparation, purification and isolation of the dioxetanes does not constitute a novel aspect of the invention disclosed and claimed herein per se.

The dioxetane is added to the sample which has been mixed with an enzyme complex which will bind to or otherwise co-act with the target analyte, if present in the sample. The dioxetane is therefore the substrate for the enzyme, the enzyme-catalyzed cleavage of the labile groups of the substrate from the body of the dioxetane resulting in the unstable oxyanion, and subsequent decomposition of the dioxetane. Where the target analyte is the enzyme itself, the dioxetane is added directly to the sample, either as drawn, or after preliminary purification to reduce turbidity. Where the target analyte is other than the trigger enzyme, the enzyme is complexed with a binding moiety, such as DNA probe or antibody, so as to bind to any target analyte present in the sample. The amount of chemiluminescence detected will be responsive both to the analyte in the sample, and the amount of analyte in the sample.

To enhance the chemiluminescent signal, and improve signal/noise ratio to permit discrimination between background signals and positive target-responsive signals at very low levels, a water-soluble enhancement agent is added to the sample prior or concomitant with the introduction of the dioxetane.

The enhancement agents of this invention, are based, in general, on polymeric onium salts, particularly quaternary salts based on phosphonium, sulfonium and, preferably, ammonium moieties. The polymers have the general formula I shown below:

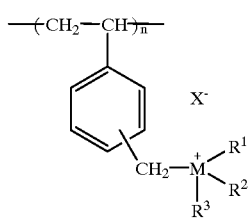

(I)

In this formula each of $R^1$, $R^2$ and $R^3$ can be a straight or branched chain unsubstituted alkyl group having from 1 to 20 carbon atoms, inclusive, e.g., methyl, ethyl, n-butyl, t-butyl, hexyl, or the like; a straight or branched chain alkyl group having from 1 to 20 carbon atoms, inclusive, substituted with one or more hydroxy, alkoxy, e.g., methoxy, ethoxy, benzyloxy or polyoxethylethoxy, aryloxy, e.g., phenoxy, amino or substituted amino, e.g., methylamino, amido, e.g., acetamido or ureido, e.g., phenyl ureido; or fluoroalkane or fluoroaryl, e.g., heptafluorobutyl, groups, an unsubstituted monocycloalkyl group having from 3 to 12 carbon ring carbon atoms, inclusive, e.g., cyclohexyl or cyclooctyl, a substituted monocycloalkyl group having from 3 to 12 ring carbon atoms, inclusive, substituted with one or more alkyl, alkoxy or fused benzo groups, e.g., methoxycyclohexyl or 1,2,3,4-tetrahydronaphthyl, a polycycloalkyl group having 2 or more fused rings, each having from 5 to 12 carbon atoms, inclusive, unsubstituted or substituted with one or more alkyl, alkoxy or aryl groups, e.g., 1-adamantyl or 3-phenyl-1-adamantyl, an aryl, alkaryl or aralkyl group having at least one ring and from 6 to 20 carbon atoms in toto, unsubstituted or substituted with one or more alkyl, aryl, fluorine or hydroxy groups, e.g., phenyl, naphthyl, pentafluorophenyl, ethylphenyl, benzyl, hydroxybenzyl, phenylbenzyl or dehydroabietyl; at least two of $R_1$, $R_2$ and $R_3$, together with the quaternary nitrogen atom to which they are bonded, can form a saturated or unsaturated, unsubstituted or substituted nitrogen-containing, nitrogen and oxygen-containing or nitrogen and sulfur-containing ring having from 3 to 5 carbon atoms, inclusive, and 1 to 3 heteroatoms, inclusive, and which may be benzoannulated, e.g., 1-pyridinium, 1-(3-alkyl or aralkyl)imidazolium, morpholino, alkyl morpholinium, alkylpiperidinium, N-acylpiperidinium, piperidino or acylpiperidino, benzoxazolium, benzthiazolium or benzamidazolium.

The symbol X represents a counterion which can include, alone or in combination, moieties such as halide, i.e., fluoride, chloride, bromide or iodide, sulfate, alkylsulfonate, e.g., methylsulfonate, arylsulfonate, e.g., p-toluenesulfonate, substituted arylsulfonate, e.g., anilinonaphthylenesulfonate (various isomers), diphenylanthracenesulfonate, perchlorate, alkanoate, e.g., acetate, arylcarboxylate, e.g., fluorescein or fluorescein derivatives, benzoheterocyclic arylcarboxylate, e.g., 7-diethylamino-4-cyanocoumarin-3-carboxylate, organic dianions such as p-terephthalate may also be represented by X.

The symbol n represents a number such that the molecular weight of such poly(vinylbenzyl quaternary ammonium salts) will range from about 500 to about 500,000 (weight average), and preferably from about 20,000 to about 70,000, as determined by intrinsic viscosity or LALLS techniques.

Methods for the preparation of these polymers, related copolymers and the related starting materials where M is nitrogen are disclosed in G. D. Jones et al, *Journal of Polymer Science*, 25, 201, 1958; in U.S. Pat. Nos. 2,780,604; 3,178,396; 3,770,439; 4,308,335; 4,340,522; 4,424,326 and German Offenlegunsschrift 2,447,611.

The symbol M may also represent phosphorous or sulfur whereupon the corresponding sulfonium or phosphonium polymers have been described in the prior art: U.S. Pat. Nos. 3,236,820 and 3,065,272.

Methods of preparation of the polymers of this invention are set forth in the referenced U.S. Patents, as well as U.S. application Ser. No. 07/811,620 and do not constitute any aspect of this invention, per se.

Copolymers containing 2 or more different pendant onium groups may also be utilized in the invention described herein.

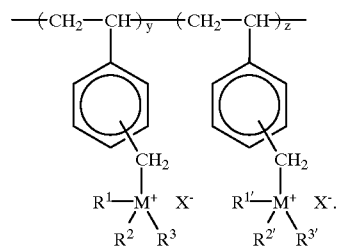

(II)

The symbols X, M', $R^{1'}$, $R^{2'}$, $R^{3'}$ are as described above for X, M, $R^1$—$R^3$. The symbols Y and Z represent the mole fraction of the individual monomers comprising the copolymer. The symbols Y and Z may thus individually vary from 0.01 to 0.99, with the sum always equalling one.

As preferred moieties, M is N, and $R^1$—$R^3$ are individually, independently, alkyl, cycloalkyl, polycycloalkyl (e.g. adamantane) aralkyl or aryl, having 1 to 20 carbon atoms, unsubstituted or further substituted with hydroxyl, amino, amido, ureido groups, or combine to form via a spiro linkage to the M atom a heterocyclic (aromatic, aliphatic or mixed, optionally including other N, S or O heteroatoms) onium moiety.

Applicants have discovered that poly (vinylbenzyltributylammonium chloride), alone, gives unpredictably superior enhancement in combination with a chemiluminescent assay based on the use of a 1,2-dioxetane reporter molecule, as described above. In point of fact, the improvement in chemiluminescent signal obtained by the addition of TBQ, alone, was generally on the order of at least twice the improvement obtained through addition of the next best enhancement agent, BDMQ. For completeness, TBQ was also evaluated, alone, versus cetyltrimethylammonium bromide, another art recognized enhancement agent.

Evaluation of TBQ Alone as an Enhancement Agent

Protocol for the evaluation of various enhancers

The enhancer samples were prepared from stock solutions in a 0.1 M diethanolamine, 1 mM $MgCl_2$, pH 9.5 buffer. CSPD or AMPPD was added to 0.5 ml of an enhancer solution (final dioxetane concentration, 0.4 mM). The background was recorded at room temperature in a Berthold 952T luminometer 10 and 60 minutes after the dioxetane addition. Subsequently, alkaline phosphatase was added (final enzyme concentration, $9.35 \times 10^{-14}$ M), and the chemiluminescent signal was measured at 10, 30 and 60 (not for all samples) minutes as a 5 sec. integral.

All buffers contained 1 mM $MgCl_2$.

**The half-time to plateau was determined as follows: 0.4 mM AMPPD in the desired buffer was preincubated at 37° C. or 30° C. and alkaline phosphatase was then added to each tube (final concentration $4.1 \times 10^{-13}$ M). The tube was inserted into a Turner model 20-E Luminometer and the half-time to steady state light emission was calculated.

TABLE 1

HALF-LIFE OF AMPPD
Effect of CTAB, TBQ, BDMQ, pH and Temperature

| | Half-Time to Plateau** | | | |
|---|---|---|---|---|
| pH | Buffer alone | + CTAB | + TBQ | + BDMQ |
| 30° C., 0.1M Sodium Carbonate | | | | |
| 9.0 | 3.66 | 17.5 | 3.48 | 4.50 |
| 9.6 | 2.07 | 9.8 | 2.79 | 2.62 |
| 10.0 | 1.62 | 7.4 | 2.17 | 2.15 |
| 30° C., 0.75M Sodium Carbonate | | | | |
| 9.0 | 4.19 | 33.5 | 6.03 | 4.84 |
| 9.6 | 2.12 | 19.3 | 4.15 | 2.82 |
| 10.0 | 1.67 | 13.3 | 2.84 | 2.27 |
| 37° C., 0.1M Sodium Carbonate | | | | |
| 9.0 | 2.37 | 10.1 | 2.53 | 2.52 |
| 9.6 | 1.34 | 5.36 | 1.65 | 1.48 |
| 10.0 | 1.06 | 4.06 | 1.29 | 1.28 |
| 37° C., 0.75M Sodium Carbonate | | | | |
| 9.0 | 2.37 | 22.0 | 3.33 | 2.81 |
| 9.6 | 1.29 | 9.6 | 2.29 | 1.62 |
| 10.0 | 0.95 | 6.5 | 1.61 | 1.33 |

TABLE 2

CHEMILUMINESCENCE OF AMPPD
SIGNAL AND BACKGROUND
Effect of CTAB, TBQ, BDMQ, pH and Temperature 30° C., 0.1 M Sodium Carbonate

| | Buffer Alone | | | Plus CTAB | | |
|---|---|---|---|---|---|---|
| pH | Back-ground* TLU | Plus Alk Phos** TLU (time to max) | S/N | Back-ground* TLU | Plus Alk Phos** TLU (time to max) | S/N |
| 9.0 | 2.0 | 55.6 (31.6) | 27.7 | 1.7 | 175.9 (93.0) | 105.9 |
| 9.6 | 2.0 | 50.7 (12.5) | 25.0 | 1.6 | 114.1 (61.5) | 69.6 |
| 10.0 | 2.0 | 30.3 (10.8) | 15.5 | 1.6 | 61.2 (42.4) | 37.3 |

| | Plus TBQ | | | Plus BDMQ | | |
|---|---|---|---|---|---|---|
| pH | Back-ground* TLU | Plus Alk Phos** TLU (time to max) | S/N | Back-ground* TLU | Plus Alk Phos** TLU (time to max) | S/N |
| 9.0 | 2.7 | 1110.8 (22.0) | 405.4 | 2.4 | 875.0 (32.0) | 372.3 |
| 9.6 | 3.8 | 1106.3 (33.8) | 294.9 | 2.1 | 559.0 (15.0) | 267.4 |
| 10.0 | 2.4 | 671.2 (18.0) | 263.2 | 2.3 | 282.8 (14.3) | 123.0 |

30° C., 0.75 M Sodium Carbonate

| | Buffer Alone | | | Plus CTAB | | |
|---|---|---|---|---|---|---|
| pH | Back-ground* TLU | Plus Alk Phos** TLU (time to max) | S/N | Back-ground* TLU | Plus Alk Phos** TLU (time to max) | S/N |
| 9.0 | 1.9 | 24.4 (30.7) | 12.6 | 1.7 | 79.1 (88.5) | 46.5 |
| 9.6 | 2.0 | 17.4 (15.4) | 8.8 | 1.7 | 42.7 (115.3) | 25.7 |
| 10.0 | 2.0 | 12.6 (9.8) | 6.4 | 1.7 | 29.2 (80.3) | 17.7 |

| | Plus TBQ | | | Plus BDMQ | | |
|---|---|---|---|---|---|---|
| pH | Back-ground* TLU | Plus Alk Phos** TLU (time to max) | S/N | Back-ground* TLU | Plus Alk Phos** TLU (time to max) | S/N |
| 9.0 | 2.0 | 254.6 (43.7) | 127.3 | 2.1 | 191.5 (27.0) | 93.0 |
| 9.6 | 2.1 | 264.2 (29.7) | 124.6 | 2.0 | 138.1 (18.6) | 70.8 |
| 10.0 | 2.1 | 272.8 (19.3) | 128.7 | 2.1 | 117.6 (12.9) | 57.1 |

37° C., 0.1 M Sodium Carbonate

| | Buffer Alone | | | Plus CTAB | | |
|---|---|---|---|---|---|---|
| pH | Back-ground* TLU | Plus Alk Phos** TLU (time to max) | S/N | Back-ground* TLU | Plus Alk Phos** TLU (time to max) | S/N |
| 9.0 | 4.1 | 70.1 (17.2) | 16.9 | 3.4 | 195.5 (53.7) | 57.5 |
| 9.6 | 4.2 | 61.6 (9.0) | 14.7 | 3.3 | 132.2 (30.7) | 40.1 |
| 10.0 | 4.1 | 41.0 (6.9) | 10.0 | 3.3 | 76.6 (22.0) | 23.2 |

| | Plus TBQ | | | Plus BDMQ | | |
|---|---|---|---|---|---|---|
| pH | Back-ground* TLU | Plus Alk Phos** TLU (time to max) | S/N | Back-ground* TLU | Plus Alk Phos** TLU (time to max) | S/N |
| 9.0 | 4.5 | 1687.4 (21.0) | 371.7 | 4.4 | 900.0 (14.2) | 204.5 |
| 9.6 | 4.4 | 1379.3 (11.4) | 314.2 | 4.6 | 578.3 (8.7) | 125.4 |
| 10.0 | 4.7 | 824.3 (7.8) | 176.9 | 4.3 | 305.8 (6.5) | 71.0 |

37° C., 0.75 M Sodium Carbonate

| | Buffer Alone | | | Plus CTAB | | |
|---|---|---|---|---|---|---|
| pH | Back-ground* TLU | Plus Alk Phos** TLU (time to max) | S/N | Back-ground* TLU | Plus Alk Phos** TLU (time to max) | S/N |
| 9.0 | 4.1 | 27.3 (14.8) | 6.6 | 3.5 | 93.4 (109.5) | 26.6 |
| 9.6 | 4.2 | 19.8 (8.2) | 4.8 | 3.4 | 51.7 (56.3) | 15.2 |
| 10.0 | 4.3 | 15.0 (5.6) | 3.5 | 3.4 | 30.3 (37.1) | 9.0 |

| | Plus TBQ | | | Plus BDMQ | | |
|---|---|---|---|---|---|---|
| pH | Back-ground* TLU | Plus Alk Phos** TLU (time to max) | S/N | Back-ground* TLU | Plus Alk Phos** TLU (time to max) | S/N |
| 9.0 | 4.2 | 410.7 (25.0) | 97.3 | 4.3 | 293.1 (18.6) | 68.8 |
| 9.6 | 4.4 | 416.0 (16.2) | 94.8 | 4.3 | 230.8 (9.0) | 53.9 |
| 10.0 | 4.2 | 402.2 (10.4) | 95.8 | 4.2 | 173.5 (6.9) | 41.4 |

As can be seen from the foregoing enhancement analysis, TBQ offers sharp improvements in chemiluminescent enhancement, and elevated S/N, as compared with the dioxetane alone, or with other art-recognized enhancement agents. Thus, the addition to the sample of TBQ, alone, provides substantial enhancement of the chemiluminescent signal and S/N values obtained. In point of fact, Applicants have found that the addition of amounts as low as below 0.005 percent down to 0.001 percent, by weight, based on the sample volume, of TBQ results in an enhancement of the chemiluminescent signal 4–5 fold over the signal obtained from the dioxetane without any enhancer.

Addition of Enhancement Agent and Enhancement Additive

The polymeric quaternary salts that constitute the enhancement agents of this invention enhance chemiluminescence in a protic environment by forming hydrophobic regions in which the dioxetane moiety, resulting from the enzyme as the oxyanion, and the subsequently formed excited state are sequestered. By providing a hydrophobic region, light-quenching water reactions are reduced or avoided all together, resulting in an overall improvement of chemiluminescence. Applicants have discovered that use of an enhancement additive, in addition to the polymeric quaternary salt enhancement agents of the claimed invention, further enhances the observed chemiluminescent signal, and improves S/N values. The enhancement additives of the claimed invention show marked improvement, in connection with the enhancement agents, at very low levels. The addition of as much as 0.005 percent, by weight, based on the sample volume, of an enhancement additive further improves the strength of the chemiluminescent signal obtained by use of the enhancement agent, while not increasing the background levels. As with the enhancement agents, the additives can be used in amounts as high as practically useful. In general, amounts greater than 50 percent, by weight, based on the sample impede assay performance. Accordingly, inclusion of both the enhancement agent, and the enhancement additive, in amounts each of 0.005 percent, by weight, based on the sample volume, up to and including a total of 50 percent, by weight, based on the sample volume, of both, are within the scope of this invention. The total of agent and additive should not exceed 50 percent.

The function of the enhancement additive is to improve the ability of the enhancement agent to form hydrophobic regions in which the dioxetane oxyanion and the resulting emitter can be sequestered, permitting decomposition and chemiluminescence in the absence of water, and therefore, reducing light-quenching reactions caused thereby. The enhancement additives can be drawn from any of a wide variety of compounds. In general, the enhancement additives may, but need not necessarily, enhance the chemiluminescent signal obtained, although not nearly so strongly as the enhancement agents of this invention. Thus, the addition of conventional surfactants, largely detergents, improves the ability of the enhancement agent to form a hydrophobic region which is relatively stable. These surfactants may be cationic, anionic, zwitterionic or neutral. Another class of enhancement additives which when added to the solution appear to improve the ability of the enhancement agent to sequester the active dioxetane species, and in any event, lead to further enhancement of the chemiluminescent signal, include negatively charged salts. A third class of enhancement additives also active at very low concentrations are conventional solvents, including a wide variety of alcohols. Another conventional solvent, turpentine, is also useful in this role.

A fourth effective class of enhancement additives are non-quaternary water-soluble polymers, such as poly(2-ethyl-Z-oxazoline), (PolyOx). While these polymers themselves may induce limited enhancement of the chemiluminescent signal without increase in background noise, when added in conjunction with the polymeric quaternary onium salt enhancement agents of this invention, sharp improvements in the chemiluminescent signal observed are obtained.

To demonstrate the improvement obtained by the addition of an enhancement additive to the enhancement agent, buffered dioxetane solutions were provided with TBQ as well as sodium dodecylbenzenesulfonate, a surfactant, poly (2-ethyl-2-oxazoline) and octyl-β-glucoside. The results, set forth below in Tables 3 and 4, are obtained with CSPD and enhancer compositions, as indicated.

ABBREVIATIONS USED IN TABLES

TBQ polyvinylbenzyltributylquaternary ammonium chloride
SDBS sodium dodecylbenzenesulfonate
PolyOx poly(2-ethyl-2-oxazoline), MW 500,000
OcGluc octyl-β-glucoside

TABLE 3

|   | TBQ, mg/ml | SDBS, mg/ml | Noise, 10 min | SIGNAL 10' | SIGNAL 30' | SDBS/TBQ SIGNAL 60' | S/N 10' | S/N 30' | S/N 60' |
| --- | --- | --- | --- | --- | --- | --- | --- | --- | --- |
| 1 | 0.00 | 0.00 | 248 | 13829 | 14699 | 14007 | 56 | 59 | 57 |
| 2 | 2.50 | 0.00 | 342 | 804468 | 1030372 | 952221 | 2352 | 3013 | 2784 |
| 3 | 1.00 | 0.00 | 369 | 870920 | 1069979 | 1037251 | 2360 | 2900 | 2811 |
| 4 | 0.50 | 0.00 | 327 | 832661 | 751145 | 691749 | 1935 | 2297 | 2115 |
| 5 | 2.50 | 0.25 | 391 | 701661 | 1761807 | 2490243 | 1795 | 4506 | 6369 |
| 6 | 1.00 | 0.10 | 403 | 958822 | 2332784 | 3060310 | 2374 | 5788 | 7594 |
| 7 | 0.50 | 0.05 | 399 | 577058 | 1410546 | 2000811 | 1446 | 3535 | 5015 |
| 8 | 2.50 | 0.50 | 431 | 854086 | 2218583 | 3826962 | 1982 | 5148 | 8879 |
| 9 | 1.00 | 0.20 | 418 | 932155 | 2245043 | 3513769 | 2241 | 5397 | 8447 |
| 10 | 0.50 | 0.10 | 413 | 797925 | 1881389 | 2834250 | 1932 | 4507 | 6863 |
| 11 | 1.00 | 0.30 | 424 | 752188 | 1908633 | 3161797 | 1774 | 4501 | 7457 |
| 12 | 0.50 | 0.15 | 401 | 847070 | 2109424 | 3392238 | 2112 | 5260 | 8459 |
| 13 | 1.00 | 0.40 | 575 | 829578 | 2217335 | 3785597 | 1443 | 3856 | 6584 |
| 14 | 0.50 | 0.20 | 418 | 722581 | 1879004 | 3094497 | 1729 | 4495 | 7403 |
| 15 | 1.00 | 0.50 | 512 | 886708 | 2310338 | 3885348 | 1732 | 4512 | 7589 |
| 16 | 0.50 | 0.25 | 518 | 827050 | 2144813 | 3579020 | 1597 | 4141 | 6909 |
| 17 | 0.75 | 0.50 | 492 | 707556 | 2012165 | 3549864 | 1438 | 4090 | 7215 |
| 18 | 0.75 | 0.25 | 524 | 732565 | 1858120 | 2959898 | 1398 | 3546 | 5649 |
| 19 | 0.75 | 0.10 | 489 | 859810 | 1968977 | 2895076 | 1758 | 4027 | 5920 |
| 20 | 0.75 | 0.05 | 456 | 873340 | 1855213 | 2384823 | 1915 | 4068 | 5188 |
| 21 | 0.50 | 0.50 | 254 | 9493 | 30130 | 56948 | 37 | 119 | 224 |
| 22 | 0.50 | 0.25 | 531 | 667565 | 1959811 | 3045419 | 1257 | 3691 | 5735 |
| 23 | 0.50 | 0.10 | 463 | 860156 | 2123923 | 3023727 | 1858 | 4587 | 6531 |
| 24 | 0.50 | 0.05 | 421 | 863325 | 1873770 | 2390762 | 2051 | 4451 | 5679 |

TABLE 4

Polyox-Detergents

| TBO, mg/ml | | | | Noise 2nd Run | Signal 10' | Signal 30' | Signal 60' | S/N 10' | S/N 30' | S/N 60' |
|---|---|---|---|---|---|---|---|---|---|---|
| 1 0.00 | | | | 236 | 14796 | 14981 | 15108 | 63 | 64 | 64 |
| 2 1.00 | | | | 313 | 707879 | 846358 | 822417 | 2262 | 2704 | 2628 |
| 3 0.50 | | | | 290 | 734283 | 830370 | 797345 | 2532 | 2863 | 2749 |
| 4 0.00 | 20 mg/ml PolyOx | | | 297 | 35058 | 39538 | 39785 | 118 | 133 | 134 |
| 5 1.00 | 20 mg/ml PolyOx | | | 589 | 1302110 | 1708716 | 1710707 | 2228 | 2913 | 2910 |
| 6 0.50 | " | | | 539 | 1430199 | 1892120 | 1851088 | 2852 | 3511 | 3432 |
| 7 0.50 | " | 5.0 mg/ml OcGluc | | 533 | 672726 | 862412 | 863895 | 1262 | 1618 | 1621 |
| 8 0.50 | " | 2.5 mg/ml OcGluc | | 432 | 894130 | 1013682 | 1047405 | 2070 | 2508 | 2425 |
| 9 0.50 | " | 1.0 mg/ml OcGluc | | 597 | 1244639 | 1585255 | 1503840 | 2015 | 2655 | 2519 |
| 10 0.50 | " | 0.5 mg/ml OcGluc | | 531 | 1333745 | 1679422 | 1801788 | 2479 | 3122 | 2988 |
| 11 0.50 | 1 mg/ml Tween 20 | 4.0 mg/ml OcGluc | 0.5 mg/ml SDBS | 255 | 16006 | 45080 | 84321 | 63 | 177 | 331 |
| 12 0.50 | " | 2.5 mg/ml OcGluc | 0.25 mg/ml SDBS | 515 | 669124 | 1676678 | 2761411 | 1299 | 3256 | 5362 |
| 13 0.50 | " | 1.0 mg/ml OcGluc | 0.1 mg/ml SDBS | 878 | 965179 | 2072592 | 2826307 | 1099 | 2361 | 3219 |
| 14 0.50 | " | 0.5 mg/ml OcGluc | 0.05 mg/ml SDBS | 770 | 916367 | 1815521 | 2278542 | 1190 | 2362 | 2959 |
| 15 1.00 | " | | 0.5 mg/ml SDBS | 669 | 1145360 | 2693529 | 4488223 | 1712 | 4026 | 6678 |
| 16 1.00 | " | | 0.25 mg/ml SDBS | 685 | 1087146 | 2341814 | 3439391 | 1587 | 3419 | 5021 |
| 17 1.00 | " | | 0.1 mg/ml SDBS | 413 | 1457360 | 2768643 | 3541193 | 3529 | 6704 | 8574 |
| 18 1.00 | " | | 0.05 mg/ml SDBS | 453 | 1091917 | 1889501 | 2266804 | 2410 | 4171 | 5004 |

As is clearly reflected in the foregoing results, the addition of a variety of enhancement additives to the TBQ enhancement agent, in varying amounts, substantially improves chemiluminescent signal and S/N.

Further improvements in chemiluminescent signal and S/N can be obtained by combining two or more additives.

As reflected in the foregoing results (Table 4), although polyox yields some nominal improvement in an enhanced signal, as an enhancement additive in connection with TBQ, improved results are obtained. It should be noted that these results were obtained according to the protocol set forth above with regard to the assessment of TBQ, using AMPPD as a dioxetane.

Improvements in enhancement are obtained by the addition of TBQ, alone, or in particular, together with an enhancement additive, independent of the dioxetane identity, provided the dioxetane is a chemiluminescent one of the type suitable for use as described above. Thus, TBQ is used efficaciously in connection with both CSPD and AMPPD. Further, as noted, enhancement additives can be used in connection with TBQ to further improve both signal strength, and S/N values. One particular enhancement additive giving excellent results in connection with TBQ and CSPD is available from DuPont Corporation, under the trademark "Zelec", sold as an anti-static agent. The composition of Zelec is believed to be maintained as a trade secret, that includes turpentine, N-octylalcohol, water, isopropyl alcohol, sodium acetate, sodium oleyl sulfate, and TS compound or compounds identified as NJ Trade Secret Registry Number 00850201001-5400P. The Material Safety Data Sheet for the Zelec anti-stat is identified by No. 5909PP. As set forth herein below, combinations of Zelec and TBQ, or TBQ copolymers, give substantial improvements and results. AMPPD and CSPD alone, as well as together with BDMQ as an enhancement agent, or in the alternative, Zelec without an enhancement agent, are included for purposes of comparison.

TABLE 5

| Dioxetane, Polymer | Noise | 10 Minutes After Enzyme | | 30 Minutes After Enzyme | |
|---|---|---|---|---|---|
| | | Signal | S/N | Signal | S/N |
| AMPPD | 424 | 108,203 | 26 | 15,173 | 36 |
| CSPD | 281 | 16,350 | 58 | 16,581 | 59 |
| AMPPD, BDMQ (1 mg/ml) | 334 | 148,273 | 444 | 273,770 | 820 |
| CSPD, TBQ (1 mg/ml) | 431 | 757,552 | 1,758 | 970,097 | 2,251 |
| AMPPD, Zelec DP (1 mg/ml) | 529 | 12,596 | 24 | 26,622 | 50 |
| AMPPD, Zelec DP (2.5 mg/ml) | 494 | 11,275 | 23 | 27,775 | 56 |
| CSPD, Zelec DP (2.5 mg/ml) | 273 | 16,687 | 61 | 31,172 | 114 |
| AMPPD, BDMQ (1 mg/ml), Zelec DP (1 mg/ml) | 725 | 363,815 | 502 | 834,997 | 1,152 |
| AMPPD, BDMQ (1 mg/ml), Zelec DP (2.5 mg/ml) | 900 | 469,637 | 522 | 1,334,310 | 1,483 |
| AMPPD, TBQ (1 mg/ml), Zelec DP (2.5 mg/ml) | 1,077 | 431,674 | 401 | 1,311,966 | 1,218 |
| CSPD, BDMQ (1 mg/ml), Zelec DP (2.5 mg/ml) | 428 | 1,119,735 | 2,616 | 2,560,207 | 5,982 |
| CSPD, TBQ (1 mg/ml), Zelec DP (2.5 mg/ml) | 508 | 1,563,198 | 3,077 | 3,836,680 | 7,553 |

Buffer: 0.1M diethanolamine, 1 mM $MgCl_2$, pH 9.5
Dioxetane concentration: 0.4 mM
Alkaline phosphatase concentration: $9.35 \times 10^{-14}$M
Luminometer: Berthold 952T
Data: 5 second RLU Combinations of Enhancement Agent and Enhancement Additive As noted previously, TBQ, alone, gives impressive improvements in observed chemiluminescence. TBQ in conjunction with an enhancement additive which improves the ability of TBQ to form hydrophobic regions in which chemiluminescent dioxetane species are sequestered further improves both chemiluminescent signal enhancement, and S/N ratio. It would of course be less desirable to improve the signal strength, if noise increased as well. The foregoing data clearly demonstrates that noise is maintained at a low level, when using commercially available dioxetanes, available from Tropix, Bedford, Mass. The improvements are far beyond those that could be expected by reason of the addition of TBQ alone, or the addition of the enhancement additive, alone, the additive occasionally having some, but generally modest, enhancement effects in the absence of the polymeric quaternary onium salt enhancement agent of the claimed invention.

To further demonstrate the improvements obtainable by using the polymeric quaternary onium salt enhancement agents of the claimed invention in combination with enhancement additives which can improve the ability of the enhancement agent to form hydrophobic regions in which chemiluminescent species are sequestered, a wide variety of combinations of enhancement agent, and one or more enhancement additives were prepared and evaluated for chemiluminescence. These enhancement agents are drawn from a wide variety of compound classes, including surfactants, negatively charged salts, conventional solvents, and water-soluble polymers. The results are reflected on the following pages.

The following method was used to evaluate various enhancer systems. Samples (0.5 ml) of each enhancer formulations were prepared from concentrated stock solutions. The buffer used was 0.1 M diethanolamine, 1 mM $MgCl_2$, pH 9.5. After the enhancer formulation was prepared, CSPD was added (final dioxetane concentration 0.04 mM). The background was then measured at room temperature in a Berthold 952T luminometer at approximately 10 minutes after substrate addition and at 1 hour. Next, alkaline phosphatase was added (final concentration, $9.35 \times 10^{-14}$ M) and the chemiluminescent signal (5 second RLU) was measured at 10, 30 and 60 (sometimes) minutes.

| Abbreviations used in tables | |
|---|---|
| AMPA-8 | aminomethylated polyacrylamide, 8% solids |
| AMPA-5 | aminomethylated polyacrylamide, 5% solids |
| AMPA-3 | aminomethylated polyacrylamide, 3% solids |
| BDMCAC | benzyldimethylcetyl ammonium chloride |
| BDMTDAC | benzyldimethyltetradetyl ammonium chloride |
| BDMQ | poly(vinylbenzyldimethylbenzyl ammonium chloride) |
| BDMQ/TBQ | BDMQ copolymerized with TBQ |
| Benz-PEI | benzylated polyethylenimine (MW 70,000) |
| BOP | benzotriazol-1-yloxytris-(dimethylamino)phosphonium hexafluorophosphate |
| CHAPS | (3-[3-cholamidopropyl)-dimethylammonio]-1-propanesulfonate) |
| CHAPSO | (3-[3-cholamidopropyl)-dimethylammonio]-2-hydroxy-1-propanesulfonate) |
| CTAB | cetyl trimethyl ammonium bromide |
| DMQ-TEQ | poly(vinylbenzyldimethyldodecyl ammonium chloride) copolymerized with poly(vinylbenzyltriethylammonium chloride) |
| HDTBPB | hexadecyltributyl phosphonium bromide |
| OcGluc | octyl-β-glucoside |
| P-DMDMPC | poly(1,1-dimethyl-3,5-dimethylene-piperidinium chloride) |
| PEI | polyethylenimine |
| PEO | poly(ethylene oxide) MW 7,000,000) |
| PO23LE | polyoxyethylene-23-lauryl ether |
| PolyOx | poly(2-ethyl-2-oxazoline) |
| PPG | polypropylene glycol |
| PTHF | poly(tetrahydrofuran) (MW 250) |
| PVA | polyvinyl alcohol |
| PVEE | poly(vinyl ethyl ether) |
| PVME | poly(vinyl methyl ether) |
| SBS | sodium benzyl sulfate |
| SDS | sodium dodecyl sulfate |
| SDBS | sodium dodecylbenzenesulfonate |
| TBQ | polyvinylbenzyltributyl ammonium chloride |
| TBQ/THQ | TBQ copolymerized with poly(vinylbenzyltrihexyl ammonium chloride) |
| TPP/TBQ | poly(vinylbenzyltriphenylphosphonium chloride) copolymerized with TBQ |
| TPP/BDMQ | poly(vinylbenzyltriphenylphosphonium chloride) copolymerized with BDMQ |

TABLE 6

CSPD

| Additive | Concentration | Noise | Signal 10 min | Signal 30 min | Signal 60 min | S/N 10 min | S/N 30 min | S/N 60 min |
|---|---|---|---|---|---|---|---|---|
| 1. none | | 282 | 17417 | 17705 | | 62 | 63 | |
| 2. BDMQ | 1 mg/ml | 536 | 369711 | 419173 | | 690 | 782 | |
| 3. TBQ | 1 mg/ml | 662 | 873852 | 1116942 | | 1320 | 1687 | |
| 4. Zelec DP<br>TBQ | 2.5 μl/ml<br>1 mg/ml | 508 | 1563198 | 3836680 | | 3077 | 7552 | |
| 5. polyvinyl alcohol<br>TBQ | 0.1 mg/ml<br>1 mg/ml | 539 | 1004417 | 1281062 | | 1863 | 2377 | |
| 6. isopropanol<br>TBQ | 1 mg/ml<br>1 mg/ml | 574 | 962628 | 1271409 | | 1677 | 2215 | |
| 7. 2-octanol<br>TBQ | 10 mg/ml<br>1 mg/ml | 568 | 1036203 | 1362463 | | 1822 | 2399 | |
| 8. Zelec DP<br>SDS<br>TBQ | 2.5 μl/ml<br>1 mg/ml<br>1 mg/ml | 927 | 837481 | 2586843 | | 903 | 1860 | |
| 9. Zelec DP<br>SDS<br>BDMQ | 2.5 μl/ml<br>1 mg/ml<br>1 mg/ml | 726 | 735959 | 2118539 | | 1014 | 2918 | |
| 10. Zelec DP<br>Tween-20<br>TBQ | 2.5 μl/ml<br>5 mg/ml<br>1 mg/ml | 853 | 594827 | 1586672 | | 697 | 1860 | |
| 11. Zelec DP<br>Tween-20<br>BDMQ | 2.5 μl/ml<br>0.01 mg/ml<br>1 mg/ml | 1129 | 545747 | 1289720 | | 483 | 1142 | |
| 12. Zelec DP<br>Tween-20<br>BDMQ | 2.5 μl/ml<br>0.05 mg/ml<br>1 mg/ml | 1112 | 545295 | 1222221 | | 490 | 1099 | |

TABLE 6-continued

CSPD

| Additive | Concentration | Noise | Signal | | | S/N | | |
|---|---|---|---|---|---|---|---|---|
| | | | 10 min | 30 min | 60 min | 10 min | 30 min | 60 min |
| 13. Zelec DP | 2.5 μl/ml | 1338 | 957409 | 2375419 | | 716 | 1775 | |
| Tween-20 | 0.01 mg/ml | | | | | | | |
| TBQ | 1 mg/ml | | | | | | | |
| 14. Zelec DP | 2.5 μl/ml | 1097 | 969399 | 2345374 | | 884 | 2138 | |
| Tween-20 | 0.05 mg/ml | | | | | | | |
| TBQ | 1 mg/ml | | | | | | | |
| 15. TBQ/THQ | 1 mg/ml | 9997 | 5429086 | 8543357 | | 543 | 855 | |
| (35 mole % THQ) | | | | | | | | |
| CTAB | 0.05 mg/ml | | | | | | | |
| 16. isopropanol | 10 mg/ml | 340 | 435740 | 533074 | | 1282 | 1568 | |
| BDMQ | 1 mg/ml | | | | | | | |
| 17. 2-octanol | 10 mg/ml | 365 | 405753 | 510671 | | 1112 | 1399 | |
| BDMQ | 1 mg/ml | | | | | | | |
| 18. Zelec DP | 3 μl/ml | 10851 | 5605794 | 9637819 | | 517 | 888 | |
| TBQ/THQ | 1 mg/ml | | | | | | | |
| (35 mole % THQ) | | | | | | | | |
| 19. AMPA-8 | 0.5 μl/ml | 385 | 297926 | 400787 | | 774 | 1041 | |
| BDMQ | 1 mg/ml | | | | | | | |
| 20. AMPA-8 | 0.5 μl/ml | 677 | 790317 | 1109404 | | 1167 | 1639 | |
| TBQ | 1 mg/ml | | | | | | | |
| 21. AMPA-5 | 0.5 μl/ml | 398 | 530827 | 624527 | | 1336 | 1569 | |
| BDMQ | 1 mg/ml | | | | | | | |
| 22. AMPA-5 | 0.5 μl/ml | 859 | 1006579 | 1289099 | | 1172 | 1501 | |
| TBQ | 1 mg/ml | | | | | | | |
| 23. AMPA-3 | 0.5 μl/ml | 564 | 194022 | 251987 | | 344 | 447 | |
| BDMQ | 1 mg/ml | | | | | | | |
| 24. AMPA-3 | 0.5 μl/ml | 796 | 757153 | 102126 | | 951 | 1283 | |
| TBQ | 1 mg/ml | | | | | | | |
| 25. TPP/TBQ | 2.5 mg/ml | 407 | 9440 | 183054 | | 232 | 450 | |
| 26. TPP/BMQ | 2.5 mg/ml | 361 | 164641 | 201410 | | 456 | 558 | |
| 27. TBQ/THQ | 1 mg/ml | 4436 | 1501695 | 3853047 | | 339 | 869 | |
| Tween-20 | 5 mg/ml | | | | | | | |
| 28. Zelec DP | 2.5 μl/ml | 8332 | 6693311 | 10215623 | | 803 | 1226 | |
| TBQ/THO | 1 mg/ml | | | | | | | |
| (35 mole % THO) | | | | | | | | |
| Tween-20 | 1 mg/ml | | | | | | | |
| 29. Zelec DP | 2.5 μl/ml | 729 | 138425 | 332143 | | 190 | 456 | |
| Tween-20 | 2.5 mg/ml | | | | | | | |
| TBQ/THQ | 1 mg/ml | | | | | | | |
| (35 mole% THO) | | | | | | | | |
| CTAB | 0.25 mg/ml | | | | | | | |
| 30. Zelec DP | 2.5 μl/ml | 402 | 633521 | 1675565 | | 1576 | 4168 | |
| TritonX100 | 0.625 mg/ml | | | | | | | |
| TBQ | 1 mg/ml | | | | | | | |
| 31. Zelec DP | 2.5 μl/ml | 381 | 673881 | 1714914 | | 1769 | 4501 | |
| Tween-80 | 1.25 mg/ml | | | | | | | |
| TBQ | 1 mg/ml | | | | | | | |
| 32. Benz-PEI | 1 mg/ml | 715 | 616720 | 1770606 | | 863 | 2630 | |
| 33. Lanoquat | 1 mg/ml | 495 | 56981 | 121737 | | 115 | 246 | |
| 34. TBQ/THQ | 0.5 mg/ml | 1574 | 5084709 | 6077275 | | 3230 | 3861 | |
| (21 mole % THQ) | | | | | | | | |
| 35. Benz-PEI | 0.5 mg/ml | 504 | 667698 | 151051 | | 1325 | 3006 | |
| BDMQ | 1 mg/ml | | | | | | | |
| 36. Lanoquat | 0.5 mg/ml | 401 | 222433 | 359929 | | 555 | 898 | |
| BDMQ | 1 mg/ml | | | | | | | |
| 37. Benz-PEI | 1 mg/ml | 858 | 745446 | 1774863 | | 869 | 2069 | |
| TBQ | 1 mg/ml | | | | | | | |
| 38. Lanoquat | 0.5 mg/ml | 570 | 600923 | 878859 | | 1054 | 1542 | |
| TBQ | 1 mg/ml | | | | | | | |
| 39. Hipofix DDD | 1 mg/ml | 418 | 346956 | 402685 | | 830 | 963 | |
| BDMQ | 1 mg/ml | | | | | | | |
| 40. Hipofix DDD | 2.5 mg/ml | 1040 | 760173 | 859718 | | 731 | 822 | |
| TBQ | 1 mg/ml | | | | | | | |
| 41. Hipofix DD-NF | 0.5 mg/ml | 343 | 345329 | 390776 | | 1007 | 1139 | |
| BDMQ | 1 mg/ml | | | | | | | |
| 42. Hipofix DD-NF | 1 mg/ml | 493 | 713154 | 854962 | | 1447 | 1734 | |
| BDMQ | 1 mg/ml | | | | | | | |
| 43. Hipolix 491 | 0.5 mg/ml | 395 | 155086 | 199658 | | 393 | 505 | |
| BDMQ | 1 mg/ml | | | | | | | |
| 44. Hipofix 491 | 0.5 mg/ml | 684 | 291815 | 366201 | | 427 | 535 | |
| TBQ | 1 mg/ml | | | | | | | |
| 45. Aerotex M-3 | 2.5 mg/ml | 449 | 197957 | 233053 | | 441 | 519 | |
| BDMQ | 1 mg/ml | | | | | | | |

TABLE 6-continued

CSPD

| | | | Signal | | | S/N | | |
|---|---|---|---|---|---|---|---|---|
| Additive | Concentration | Noise | 10 min | 30 min | 60 min | 10 min | 30 min | 60 min |
| 46. Aerotex M-3 | 5 mg/ml | 791 | 492405 | 527229 | | 623 | 723 | |
| TBQ | 1 mg/ml | | | | | | | |
| 47. PVEE (lo mw) | 1 mg/ml | 568 | 2372633 | 378368 | | 418 | 666 | |
| BDMQ | 1 mg/ml | | | | | | | |
| 48. PVEE (lo mw) | 1 mg/ml | 655 | 730024 | 1151041 | | 1115 | 1757 | |
| TBQ | 1 mg/ml | | | | | | | |
| 49. Polyox (mw 50K) | 1 mg/ml | 574 | 342402 | 422461 | | 597 | 740 | |
| BDMQ | 1 mg/ml | | | | | | | |
| 50. Polyox (mw 50K) | 1 mg/ml | 699 | 1284452 | 1587003 | | 1838 | 2270 | |
| TBQ | 1 mg/ml | | | | | | | |
| 51. PVME | 1.25 mg/ml | 917 | 309446 | 371819 | | 337 | 405 | |
| BDMQ | 1 mg/ml | | | | | | | |
| 52. PVME | 1.25 mg/ml | 834 | 663814 | 839470 | | 796 | 1007 | |
| TBQ | 1 mg/ml | | | | | | | |
| 53. PTHF (mw 250) | 2.5 mg/ml | 700 | 265174 | 352224 | | 379 | 503 | |
| BDMQ | 1 mg/ml | | | | | | | |
| 54. PTHF (mw 250) | 0.5 mg/ml | 758 | 634639 | 851396 | | 837 | 1123 | |
| TBQ | 1 mg/ml | | | | | | | |
| 55. Polyox(mw 500K) | 0.5 mg/ml | 1699 | 316630 | 385553 | | 453 | 552 | |
| BDMQ | 1 mg/ml | | | | | | | |
| 56. Polyox(mw 500K) | 5 mg/ml | 889 | 628735 | 822133 | | 707 | 925 | |
| TBQ | 1 mg/ml | | | | | | | |
| 57. PEO | 1 mg/ml | 670 | 220386 | 257387 | | 329 | 384 | |
| BDMQ | 1 mg/ml | | | | | | | |
| 58. PEO | 1 mg/ml | 776 | 541518 | 695872 | | 698 | 897 | |
| TBQ | 1 mg/ml | | | | | | | |
| 59. CelquatH100 | 0.5 mg/ml | 406 | 284794 | 353576 | | 701 | 871 | |
| BDMQ | 1 mg/ml | | | | | | | |
| 60. CelquatH100 | 0.5 mg/ml | 719 | 734280 | 970599 | | 1021 | 1350 | |
| TBQ | 1 mg/ml | | | | | | | |
| 61. Celquat L200 | 0.5 mg/ml | 499 | 268280 | 326627 | | 537 | 655 | |
| BDMQ | 1 mg/ml | | | | | | | |
| 62. CelquatL200 | 0.5 mg/ml | 969 | 722551 | 928806 | | 746 | 959 | |
| TBQ | 1 mg/ml | | | | | | | |
| 63. CelquatSC240 | 0.5 mg/ml | 530 | 317199 | 382101 | | 598 | 721 | |
| BDMQ | 1 mg/ml | | | | | | | |
| 64. CelquatSC240 | 1 mg/ml | 804 | 811714 | 1030836 | | 1010 | 1282 | |
| TBQ | 1 mg/ml | | | | | | | |
| 65. Pluronic122 | 0.5 mg/ml | 608 | 47854 | 117319 | | 79 | 193 | |
| BDMQ | 1 mg/ml | | | | | | | |
| 66. Pluronic122 | 1 mg/ml | 746 | 66584 | 181683 | | 89 | 244 | |
| TBQ | 1 mg/ml | | | | | | | |
| 67. Pluronic123 | 0.5 mg/ml | 648 | 69686 | 150161 | | 106 | 232 | |
| BDMQ | 1 mg/ml | | | | | | | |
| 68. Pluronic123 | 0.5 mg/ml | 1453 | 178632 | 386930 | | 123 | 266 | |
| TBQ | 1 mg/ml | | | | | | | |
| 69. Pluronic150R1 | 0.5 mg/ml | 896 | 156254 | 173414 | | 174 | 194 | |
| BDMQ | 1 mg/ml | | | | | | | |
| 70. Pluronic150R1 | 0.5 mg/ml | 1996 | 285940 | 324257 | | 143 | 162 | |
| TBQ | 1 mg/ml | | | | | | | |
| 71. CHAPS | 0.5 mg/ml | 210 | 14326 | 42519 | | 68 | 202 | |
| 72. CHAPSO | 0.5 mg/ml | 218 | 15119 | 42489 | | 69 | 195 | |
| 73. Zelec DP | 2.25 μl/ml | 638 | 741248 | 1616666 | | 1162 | 2534 | |
| CHAPS | 1 mg/ml | | | | | | | |
| BDMQ | | | | | | | | |
| 74. Zelec DP | 2.25 mg/ml | 858 | 1146672 | 2754178 | | 1336 | 3210 | |
| CHAPS | 1 mg/ml | | | | | | | |
| TBQ | 1 mg/ml | | | | | | | |
| 75. Zelec DP | 2.25 μl/ml | 555 | 718553 | 1530910 | | 1295 | 2758 | |
| CHAPSO | 1 mg/ml | | | | | | | |
| BDMQ | 1 mg/ml | | | | | | | |
| 76. Zelec DP | 2.25 mg/ml | 900 | 1090555 | 2453191 | | 1212 | 2726 | |
| CHAPSO | 1 mg/ml | | | | | | | |
| TBQ | 1 mg/ml | | | | | | | |
| 77. Polybrene | 5 mg/ml | 413 | 19740 | 24261 | | 48 | 59 | |
| CHAPS | 5 mg/ml | | | | | | | |
| 78. Polybrene | 5 mg/ml | 2853 | 486059 | 705032 | | 170 | 247 | |
| CHAPS | 5 mg/ml | | | | | | | |
| BDMQ | 1 mg/ml | | | | | | | |
| 79. Polybrene | 1 mg/ml | 5982 | 683646 | 839733 | | 114 | 140 | |
| CHAPS | 1 mg/ml | | | | | | | |
| BDMQ | 1 mg/ml | | | | | | | |
| 80. Polybrene | 5 mg/ml | 6348 | 832574 | 1239584 | | 131 | 195 | |

TABLE 6-continued

CSPD

| | | | Signal | | | S/N | | |
|---|---|---|---|---|---|---|---|---|
| Additive | Concentration | Noise | 10 min | 30 min | 60 min | 10 min | 30 min | 60 min |
| CHAPSO | 5 mg/ml | | | | | | | |
| BDMQ | 1 mg/ml | | | | | | | |
| 81. Polybrene | 0.5 mg/ml | 6441 | 736510 | 897356 | | 114 | 139 | |
| CHAPSO | 0.5 mg/ml | | | | | | | |
| BDMQ | 1 mg/ml | | | | | | | |
| 82. BenzethoniumCl | 0.5 mg/ml | 692 | 34183 | 81211 | | 49 | 117 | |
| 83. BDMQ/TBQ | 1 mg/ml | 568 | 742480 | 859880 | | 1307 | 1514 | |
| (20% BDMQ) | | | | | | | | |
| 84. BDMQ/TBQ | 1 mg/ml | 740 | 927108 | 1113083 | | 1253 | 1504 | |
| (10% BDMQ) | | | | | | | | |
| 85. Zelec DP | 2.5 μl/ml | 1910 | 899187 | 1768511 | | 471 | 926 | |
| BDMQ/TBQ | 1 mg/ml | | | | | | | |
| (20% BDMQ) | | | | | | | | |
| 86. Zelec DP | 2.5 μl/ml | 8392 | 1057422 | 2177684 | | 126 | 259 | |
| BDMQ/TBQ | 1 mg/ml | | | | | | | |
| (10% BDMQ) | | | | | | | | |
| 87. Avitex ML | 0.5 mg/ml | 1051 | 142640 | 298297 | | 136 | 284 | |
| BDMQ | 1 mg/ml | | | | | | | |
| 88. Avitex ML | 0.5 mg/ml | 1318 | 466655 | 866897 | | 354 | 658 | |
| TBQ | 1 mg/ml | | | | | | | |
| 89. Polyox(500K) | 0.5 mg/ml | 1730 | 862023 | 1239458 | | 498 | 716 | |
| CTAB | 0.01 mg/ml | | | | | | | |
| TBQ | 1 mg/ml | | | | | | | |
| 90. Polyox(50K) | 0.5 mg/ml | 952 | 872307 | 1183521 | | 916 | 1243 | |
| CTAB | 0.01 mg/ml | | | | | | | |
| TBQ | 1 mg/ml | | | | | | | |
| 91. Agefloc B50 | 0.5 mg/ml | 952 | 872307 | 1183521 | | 1961 | 2262 | |
| TBQ | 1 mg/ml | | | | | | | |
| 92. Agefloc B50 | 0.5 mg/ml | 574 | 308582 | 347312 | | 538 | 605 | |
| BDMQ | 1 mg/ml | | | | | | | |
| 93. Agefloc A50 | 1 mg/ml | 689 | 1015523 | 1225260 | | 1474 | 1778 | |
| TBQ | 1 mg/ml | | | | | | | |
| 94. Agefloc A50 | 0.5 mg/ml | 693 | 309616 | 355165 | | 447 | 513 | |
| TBQ | 1 mg/ml | | | | | | | |
| 95. Agefloc A50HV | 0.5 mg/ml | 1265 | 1190551 | 1343823 | | 941 | 1062 | |
| TBQ | 1 mg/ml | | | | | | | |
| 96. Agefloc A50HV | 0.5 mg/ml | 769 | 284170 | 325540 | | 370 | 423 | |
| TBQ | 1 mg/ml | | | | | | | |
| 97. SDBS | 0.5 mg/ml | 725 | 758078 | 2071149 | | 1046 | 2857 | |
| Tween-20 | 20 mg/ml | | | | | | | |
| BDMQ | 1 mg/ml | | | | | | | |
| 98. SDBS | 0.5 mg/ml | 668 | 638270 | 1763156 | | 955 | 2639 | |
| Triton X-100 | 1 mg/ml | | | | | | | |
| BDMQ | 1 mg/ml | | | | | | | |
| 99. SDBS | 0.5 mg/ml | 1337 | 1021526 | 2582544 | | 764 | 1932 | |
| CHAPS | 1 mg/ml | | | | | | | |
| BDMQ | 1 mg/ml | | | | | | | |
| 100. SDBS | 0.5 mg/ml | 1476 | 940142 | 2282165 | | 637 | 1546 | |
| CHAPSO | 1 mg/ml | | | | | | | |
| BDMQ | 1 mg/ml | | | | | | | |
| 101. SDBS | 0.5 mg/ml | 1329 | 883203 | 2195667 | | 665 | 1652 | |
| CTAB | 0.05 mg/ml | | | | | | | |
| BDMQ | 1 mg/ml | | | | | | | |
| 102. DAXAD | 1 mg/ml | 866 | 1059832 | 1225160 | | 1224 | 1415 | |
| TBQ | 1 mg/ml | | | | | | | |
| 103. DAXAD | 0.5 mg/ml | 802 | 771273 | 833134 | | 962 | 1039 | |
| BDMQ/TBQ | 1 mg/ml | | | | | | | |
| (20% BDMQ) | | | | | | | | |
| 104. DAXAD | 0.5 mg/ml | 510 | 301223 | 351656 | | 591 | 690 | |
| BDMQ | 1 mg/ml | | | | | | | |
| 105. DextranSul | 0.5 mg/ml | 306 | 37132 | 39345 | | 121 | 129 | |
| BDMQ | 0.1 mg/ml | | | | | | | |
| 106. SDS | 0.6 mg/ml | 961 | 772634 | 2258788 | | 804 | 2350 | |
| Tween-20 | 1 mg/ml | | | | | | | |
| TBQ | 1 mg/ml | | | | | | | |
| 107 SDS | 0.6 mg/ml | 1100 | 867025 | 2581024 | | 788 | 2346 | |
| Triton X-100 | 1 mg/ml | | | | | | | |
| TBQ | 1 mg/ml | | | | | | | |
| 108. SDS | 0.6 mg/ml | 721 | 592457 | 1575837 | | 822 | 2186 | |
| Tween-20 | 1 mg/ml | | | | | | | |
| BDMQ | 1 mg/ml | | | | | | | |

TABLE 6-continued

CSPD

| Additive | Concentration | Noise | Signal 10 min | Signal 30 min | Signal 60 min | S/N 10 min | S/N 30 min | S/N 60 min |
|---|---|---|---|---|---|---|---|---|
| 109. SDS | 0.6 mg/ml | 697 | 412432 | 1143741 | | 592 | 1641 | |
| Triton X-100 | 1 mg/ml | | | | | | | |
| BDMQ | 1 mg/ml | | | | | | | |
| 110. SDBS | 0.1 mg/ml | 2097 | 957195 | 2016212 | | 456 | 962 | |
| Tween-20 | 1 mg/ml | | | | | | | |
| octyl-glucoside | 1 mg/ml | | | | | | | |
| TBQ | 1 mg/ml | | | | | | | |
| 111. SDBS | 0.1 mg/ml | 2276 | 924169 | 2002195 | | 406 | 880 | |
| Triton X-100 | 1 mg/ml | | | | | | | |
| octyl-glucoside | 1 mg/ml | | | | | | | |
| TBQ | 1 mg/ml | | | | | | | |
| 112. SDBS | 0.5 mg/ml | 288 | 22720 | 56363 | | 79 | 196 | |
| Tween-20 | 1 mg/ml | | | | | | | |
| CTAB | 1 mg/ml | | | | | | | |
| TBQ | 1 mg/ml | | | | | | | |
| 113. SDBS | 0.5 mg/ml | 291 | 17291 | 43494 | | 59 | 149 | |
| Triton-X-100 | 1 mg/ml | | | | | | | |
| CTAB | 1 mg/ml | | | | | | | |
| TBQ | 1 mg/ml | | | | | | | |
| 114. SDBS | 0.5 mg/ml | 231 | 34158 | 101381 | | 148 | 439 | |
| Tween-20 | 1 mg/ml | | | | | | | |
| BDMCAC | 1 mg/ml | | | | | | | |
| TBQ | 1 mg/ml | | | | | | | |
| 115. SDBS | 0.5 mg/ml | 233 | 31723 | 90256 | | 136 | 387 | |
| Triton X-100 | 1 mg/ml | | | | | | | |
| BDMCAC | 1 mg/ml | | | | | | | |
| TBQ | 1 mg/ml | | | | | | | |
| 116. SDBS | 0.1 mg/ml | 878 | 1052025 | 2086077 | | 1198 | 2376 | |
| Tween-20 | 1 mg/ml | | | | | | | |
| CTAB | 0.1 mg/ml | | | | | | | |
| TBQ | 1 mg/ml | | | | | | | |
| 117. SDBS | 0.1 mg/ml | 1009 | 1358360 | 2551569 | | 1346 | 2529 | |
| Tween-20 | 1 mg/ml | | | | | | | |
| CTAB | 0.01 mg/ml | | | | | | | |
| TBQ | 1 mg/ml | | | | | | | |
| 118. CTAB | 0.1 mg/ml | 412 | 395868 | 714210 | | 961 | 1734 | |
| Triton X-100 | 1 mg/ml | | | | | | | |
| TBO | 1 mg/ml | | | | | | | |
| 119. CTAB | 0.01 mg/ml | 632 | 727582 | 1089538 | | 1151 | 1724 | |
| Tnton X-100 | 1 mg/ml | | | | | | | |
| TBQ | 1 mg/ml | | | | | | | |
| 120. octyl-glucoside | 1 mg/ml | 586 | 726013 | 836153 | | 1239 | 1427 | |
| TBO | 1 mg/ml | | | | | | | |
| 121. Tween-20 | 1 mg/ml | 550 | 371246 | 620097 | | 675 | 1128 | |
| TBQ | 1 mg/ml | | | | | | | |
| 122. TritonX-100 | 1 mg/ml | 636 | 329832 | 570539 | | 519 | 897 | |
| TBQ | 1 mg/ml | | | | | | | |
| 123. CTAB | 1 mg/ml | 227 | 15217 | 26636 | | 67 | 117 | |
| TBQ | 1 mg/ml | | | | | | | |
| 124. Polyox(50K) | 20 mg/ml | 154 | 26179 | 47219 | | 170 | 307 | |
| CTAB | 0.25 mg/ml | | | | | | | |
| 125. Polyox(50K) | 20 mg/ml | 243 | 495112 | 723580 | | 2037 | 2978 | |
| CTAB | 0.25 mg/ml | | | | | | | |
| TBQ | 1 mg/ml | | | | | | | |
| 126. Polyox(50K) | 20 mg/ml | 607 | 768812 | 930826 | | 1267 | 1533 | |
| CTAB | 0.025 mg/ml | | | | | | | |
| TBQ | 1 mg/ml | | | | | | | |
| 127. Polyox(50K) | 20 mg/ml | 402 | 832297 | 962123 | | 2070 | 2393 | |
| CTAB | 0.0025 mg/ml | | | | | | | |
| TBO | 1 mg/ml | | | | | | | |
| 128. Polyox(50K) | 0.5 mg/ml | 391 | 970406 | 1102900 | | 2462 | 2821 | |
| TBQ | 1 mg/ml | | | | | | | |
| 129. Polyox(500K) | 20 mg/ml | 283 | 42628 | 77784 | | 151 | 275 | |
| CTAB | 0.25 mg/ml | | | | | | | |
| 130. Polyox(500K) | 20 mg/ml | 275 | 36981 | 44021 | | 134 | 160 | |
| CTAB | 0.025 mg/ml | | | | | | | |
| 131. Polyox(500K) | 20 mg/ml | 250 | 40563 | 45500 | | 162 | 182 | |
| CTAB | 0.0025 mg/ml | | | | | | | |
| 132. Polyox(500K) | 1 mg/ml | 397 | 1527695 | 1781760 | | 3848 | 4488 | |
| CTAB | 0.05 mg/ml | | | | | | | |
| TBQ | 1 mg/ml | | | | | | | |

TABLE 6-continued

| | | | Signal CSPD | | | S/N | | |
|---|---|---|---|---|---|---|---|---|
| Additive | Concentration | Noise | 10 min | 30 min | 60 min | 10 min | 30 min | 60 min |
| 133. Polyox(500K) | 1 mg/ml | 455 | 1629263 | 1834806 | | 3581 | 4033 | |
| CTAB | 0.005 mg/ml | | | | | | | |
| TBQ | 1 mg/ml | | | | | | | |
| 134. Polyox(500K) | 1 mg/ml | 514 | 1635987 | 1823578 | | 3183 | 3548 | |
| CTAB | 0.0005 mg/ml | | | | | | | |
| TBQ | 1 mg/ml | | | | | | | |
| 135. Polyox(500K) | 20 mg/ml | 623 | 2505788 | 3072392 | | 4022 | 4931 | |
| TBQ | 1 mg/ml | | | | | | | |
| 136. Polyox(500K) | 20 mg/ml | 432 | 528833 | 653731 | 669867 | 1224 | 1513 | 1551 |
| BDMQ | 1 mg/ml | | | | | | | |
| 137. Polyox(500K) | 20 mg/ml | 17614 | 2047964 | 4050329 | | 116 | 230 | |
| Zelec DP | 2.5 µl/ml | | | | | | | |
| Tween-20 | 0.625 mg/ml | | | | | | | |
| TBQ | 1 mg/ml | | | | | | | |
| 138. Polyox(500K) | 20 mg/ml | 562 | 76352 | 229205 | | 136 | 408 | |
| SDBS | 0.5 mg/ml | | | | | | | |
| CTAB | 0.75 mg/ml | | | | | | | |
| Tween-20 | 1 mg/ml | | | | | | | |
| TBQ | 1 mg/ml | | | | | | | |
| 139. Polyox(500K) | 20 mg/ml | 2689 | 474537 | 1267603 | | 176 | 471 | |
| SDBS | 0.5 mg/ml | | | | | | | |
| CTAB | 0.5 mg/ml | | | | | | | |
| Tween-20 | 1 mg/ml | | | | | | | |
| TBQ | 1 mg/ml | | | | | | | |
| 140. Polyox(500K) | 20 mg/ml | 5476 | 675082 | 1535300 | | 123 | 280 | |
| SDBS | 0.25 mg/ml | | | | | | | |
| CTAB | 0.3 mg/ml | | | | | | | |
| Tween-20 | 1 mg/ml | | | | | | | |
| TBQ | 1 mg/ml | | | | | | | |
| 141. Polyox(500K) | 20 mg/ml | 729 | 393791 | 507399 | | 540 | 696 | |
| 1M NaCl in DEA | | | | | | | | |
| TBQ | 1 mg/ml | | | | | | | |
| 142. Polyox(500K) | 20 mg/ml | 714 | 444112 | 545624 | | 622 | 764 | |
| 0.5M NaCl in DEA | | | | | | | | |
| TBQ | 1 mg/ml | | | | | | | |
| 143. Polyox(500K) | 20 mg/ml | 803 | 271814 | 311794 | | 338 | 388 | |
| 1M NaCl (no DEA) | | | | | | | | |
| TBQ | 1 mg/ml | | | | | | | |
| 144. Polyox(500K) | 20 mg/ml | 723 | 316032 | 342073 | | 437 | 473 | |
| 0.5M NaCl (no DEA) | | | | | | | | |
| TBQ | 1 mg/ml | | | | | | | |
| 145. Polyox(500K) | 20 mg/ml | 810 | 1255809 | 2567260 | | 1550 | 2388 | |
| SDBS | 0.1 mg/ml | | | | | | | |
| Chaps | 1 mg/ml | | | | | | | |
| Tween-20 | 1 mg/ml | | | | | | | |
| TBQ | 1 mg/ml | | | | | | | |
| 146. Polyox(500K) | 20 mg/ml | 858 | 1529784 | 3035681 | | 1783 | 2575 | |
| SDBS | 0.1 mg/ml | | | | | | | |
| Chapso | 1 mg/ml | | | | | | | |
| Tween-20 | 1 mg/ml | | | | | | | |
| TBQ | 1 mg/ml | | | | | | | |
| 147. Polyox(500K) | 20 mg/ml | 1309 | 1581194 | 3072325 | | 1208 | 1674 | |
| SDBS | 0.1 mg/ml | | | | | | | |
| Chaps | 1 mg/ml | | | | | | | |
| Triton-X100 | 1 mg/ml | | | | | | | |
| TBQ | 1 mg/ml | | | | | | | |
| 148. Polyox(500K) | 20 mg/ml | 2593 | 1240847 | 2249328 | | 479 | 591 | |
| SDBS | 0.05 mg/ml | | | | | | | |
| Chapso | 0.5 mg/ml | | | | | | | |
| Tween-20 | 1 mg/ml | | | | | | | |
| TBQ | 1 mg/ml | | | | | | | |
| 149. Polybrene | 0.5 mg/ml | 425 | 979550 | 1210591 | | 2305 | 2848 | |
| TBQ | 1 mg/ml | | | | | | | |
| 150. Polyox(500K) | 20 mg/ml | 506 | 1106515 | 1378277 | | 2187 | 2724 | |
| Polybrene | 0.5 mg/ml | | | | | | | |
| TBQ | 1 mg/ml | | | | | | | |
| 151. Polyox(500K) | 20 mg/ml | 765 | 995361 | 1202025 | | 1301 | 1571 | |
| CHAPS | 0.5 mg/ml | | | | | | | |
| Polybrene | 0.5 mg/ml | | | | | | | |
| TBQ | 1 mg/ml | | | | | | | |
| 152. Polyox(500K) | 20 mg/ml | 2024 | 1149546 | 1385744 | | 568 | 685 | |
| CHAPSO | 0.5 mg/ml | | | | | | | |

TABLE 6-continued

CSPD

| | Additive | Concentration | Noise | Signal 10 min | Signal 30 min | Signal 60 min | S/N 10 min | S/N 30 min | S/N 60 min |
|---|---|---|---|---|---|---|---|---|---|
| | Polybrene | 0.5 mg/ml | | | | | | | |
| | TBQ | 1 mg/ml | | | | | | | |
| 153. | Polybrene | 0.5 mg/ml | 567 | 1144898 | 1337005 | | 2019 | 2358 | |
| | CHAPS | 0.5 mg/ml | | | | | | | |
| | TBQ | 1 mg/ml | | | | | | | |
| 154. | Polybrene | 0.5 mg/ml | 665 | 1240889 | 1442628 | | 1866 | 2169 | |
| | CHAPSO | 0.5 mg/ml | | | | | | | |
| | TBQ | 1 mg/ml | | | | | | | |
| 155. | Polyox(500K) | 20 mg/ml | 573 | 766172 | 942697 | | 1337 | 1646 | |
| | DEA/Carb buffer 9.5 | | | | | | | | |
| | TBQ | 1 mg/ml | | | | | | | |
| 156. | TBQ | 1 mg/ml | 466 | 320952 | 371408 | | 689 | 797 | |
| | DEA/Carb buffer 9.5 | | | | | | | | |
| 157. | Polyox(500K) | 20 mg/ml | 531 | 1996396 | 2509803 | | 3760 | 4727 | |
| | TBQ | 0.5 mg/ml | | | | | | | |
| 158. | Polyox(500K) | 20 mg/ml | 482 | 1649504 | 2021238 | | 3422 | 4193 | |
| | octyl-glucoside | 1 mg/ml | | | | | | | |
| | TBQ | 1 mg/ml | | | | | | | |
| 159. | Polyox(500K) | 20 mg/ml | 262 | 35061 | 36818 | | 134 | 141 | |
| | octyl-glucoside | 5 mg/ml | | | | | | | |
| 160. | Polyox(500K) | 20 mg/ml | 604 | 1729994 | 2149082 | | 2864 | 3558 | |
| | phenyl-glucoslde | 5 mg/ml | | | | | | | |
| | TBQ | 1 mg/ml | | | | | | | |
| 161. | Polyox(500K) | 20 mg/ml | 268 | 30705 | 33366 | | 150 | 124 | |
| | phenyl-glucoside | 5 mg/ml | | | | | | | |
| 162. | Polyox(500K) | 20 mg/ml | 562 | 1372766 | 2935468 | | 2443 | 5223 | |
| | octyl-glucoside | 2.5 mg/ml | | | | | | | |
| | SDBS | 0.25 mg/ml | | | | | | | |
| | Tween-20 | 1 mg/ml | | | | | | | |
| | TBQ | 1 mg/ml | | | | | | | |
| 163. | Polyox(500K) | 20 mg/ml | 632 | 1197951 | 2459440 | | 1895 | 3892 | |
| | ph.enyl-glucoside | 2.5 mg/ml | | | | | | | |
| | SDBS | 0.25 mg/ml | | | | | | | |
| | Tween-20 | 1 mg/ml | | | | | | | |
| | TBQ | 1 mg/ml | | | | | | | |
| 164. | SDBS | 0.1 mg/ml | 413 | 1457360 | 2768643 | 3541193 | 3529 | 6704 | 8574 |
| | Tween-20 | 1 mg/ml | | | | | | | |
| | TBQ | 1 mg/ml | | | | | | | |
| 165. | SDBS | 0.1 mg/ml | 414 | 1353062 | 2649803 | 3601796 | 3268 | 6400 | 8700 |
| | Tween-20 | 1 mg/ml | | | | | | | |
| | TBQ | 0.5 mg/ml | | | | | | | |
| 166. | SBS | 1 mg/ml | 318 | 405862 | 478723 | 473862 | 1276 | 1505 | 1490 |
| | BDMQ | 1 mg/ml | | | | | | | |
| 167. | SBS | 0.5 mg/ml | 341 | 950755 | 1115291 | 1107561 | 2788 | 3271 | 3248 |
| | TBQ | 1 mg/ml | | | | | | | |

TABLE 7

AMPPD

| | Additive | Concentration | Noise | Signal 10 min | Signal 30 min | Signal 60 min | S/N 10 min | S/N 30 min | S/N 60 min |
|---|---|---|---|---|---|---|---|---|---|
| 1. | none | | 601 | 15434 | 22361 | | 26 | 37 | |
| 2. | BDMQ | 1 mg/ml | 1021 | 239457 | 392753 | | 250 | 410 | |
| 3. | TBQ | 1 mg/ml | 1940 | 529838 | 953548 | | 311 | 819 | |
| 4. | TBQ/THQ | 1 mg/ml | 10112 | 3909328 | 7854723 | | 387 | 777 | |
| 5. | BDMCAC | 0.5 mg/ml | 539 | 19978 | 59936 | | 39 | 118 | |
| 6. | THQ monomer | 5 mg/ml | 611 | 38535 | 92199 | | 58 | 140 | |
| 7. | Andogen 464 | 1 mg/ml | 1019 | 232240 | 713917 | | 253 | 779 | |
| 8. | Andogen 464 | 5 mg/ml | 447 | 19223 | 63303 | | 43 | 214 | |
| | Triton X-100 | 10 mg/ml | | | | | | | |
| 9. | Andogen 464 | 5 mg/ml | 784 | 49888 | 167538 | | 64 | 214 | |
| | Triton X-100 | 1 mg/ml | | | | | | | |
| 10. | Andogen 464 | 5 mg/ml | 493 | 32050 | 107977 | | 65 | 219 | |
| | Tween-20 | 10 mg/ml | | | | | | | |
| 11. | Andogen 464 | 1 mg/ml | 718 | 39265 | 131675 | | 55 | 183 | |
| | Tween-20 | 1 mg/ml | | | | | | | |
| 12. | BDMTDAC | 0.1 mg/ml | 1213 | 94008 | 210047 | | 78 | 173 | |

TABLE 7-continued

AMPPD

| | Additive | Concentration | Noise | Signal 10 min | Signal 30 min | Signal 60 min | S/N 10 min | S/N 30 min | S/N 60 min |
|---|---|---|---|---|---|---|---|---|---|
| | BDMQ | 1 mg/ml | | | | | | | |
| 13. | BDMDAB | 0.1 mg/ml | 1366 | 156795 | 273187 | | 115 | 200 | |
| | BDMQ | 1 mg/ml | | | | | | | |
| 14. | Zonyl Surf. | 0.1 mg/ml | 1597 | 170683 | 283296 | | 107 | 177 | |
| | BDMQ | 1 mg/ml | | | | | | | |
| 15. | BDMTDAC | 0.1 mg/ml | 752 | 186443 | 432829 | | 248 | 576 | |
| | TBQ | 1 mg/ml | | | | | | | |
| 16. | BDMDAB | 0.1 mg/ml | 1000 | 379583 | 717087 | | 380 | 717 | |
| | TBQ | 1 mg/ml | | | | | | | |
| 17. | Zonyl Surf. | 0.1 mg/ml | 1108 | 393546 | 734506 | | 355 | 663 | |
| | TBQ | 1 mg/ml | | | | | | | |
| 18. | octyl-glucoside | 0.1 mg/ml | 1474 | 167319 | 316876 | | 35 | 68 | |
| | BDMQ | 1 mg/ml | | | | | | | |
| 19. | phenyl-glucoside | 0.1 mg/ml | 1663 | 168296 | 31431 | | 101 | 189 | |
| | BDMQ | 1 mg/ml | | | | | | | |
| 20. | octyl-glucoside | 1 mg/ml | 359 | 16800 | 41762 | | 47 | 116 | |
| | BDMDAB | 1 mg/ml | | | | | | | |
| | BDMQ | 1 mg/ml | | | | | | | |
| 21. | octyl-glucoside | 0.5 mg/ml | 1000 | 339007 | 648072 | | 339 | 648 | |
| | TBQ | 1 mg/ml | | | | | | | |
| 22. | phenyl-glucoside | 0.5 mg/ml | 1221 | 269016 | 545848 | | 220 | 439 | |
| | TBQ | 1 mg/ml | | | | | | | |
| 23. | HDTBPB | 0.5 mg/ml | 1412 | 36919 | 102172 | | 26 | 72 | |
| 24. | Andogen 464 | 1 mg/ml | 3919 | 223888 | 682817 | | 57 | 174 | |
| | phenyl-glucoside | 1 mg/ml | | | | | | | |
| 25. | HDTBPB | 0.5 mg/ml | 640 | 40379 | 124470 | | 63 | 195 | |
| | phenyl-glucoside | 1 mg/ml | | | | | | | |
| 26. | Nonidet P-400 | 1 mg/ml | 1143 | 112668 | 252316 | | 99 | 221 | |
| | BDMQ | 1 mg/ml | | | | | | | |
| 27. | Tween-80 | 0.5 mg/ml | 844 | 87136 | 165285 | | 103 | 196 | |
| | BDMQ | 1 mg/ml | | | | | | | |
| 28. | PO23LE | 0.1 mg/ml | 1980 | 130369 | 261388 | | 66 | 132 | |
| | BDMQ | 1 mg/ml | | | | | | | |
| 29. | Ipegal | 0.5 mg/ml | 822 | 116303 | 231011 | | 142 | 281 | |
| | BDMQ | 1 mg/ml | | | | | | | |
| 30. | HDTBPB | 0.1 mg/ml | 1167 | 35861 | 90738 | | 31 | 78 | |
| | BDMQ | 1 mg/ml | | | | | | | |
| 31. | β-cyclodex. | 0.5 mg/ml | 451 | 46605 | 101249 | | 103 | 224 | |
| | BDMQ | 1 mg/ml | | | | | | | |
| 32. | FC-135 | 0.5 mg/ml | 420 | 66398 | 133292 | | 158 | 317 | |
| | BDMQ | 1 mg/ml | | | | | | | |
| 33. | BOP | 1 mg/ml | 3327 | 464178 | 1059036 | | 140 | 318 | |
| | BDMQ | 1 mg/ml | | | | | | | |
| 34. | PPG | 1 mg/ml | 803 | 25376 | 411277 | | 316 | 512 | |
| | BDMQ | 1 mg/ml | | | | | | | |
| 35. | PEI | 0.1 mg/ml | 771 | 265606 | 446988 | | 345 | 580 | |
| | BDMQ | 1 mg/ml | | | | | | | |
| 36. | P-DMDMPC | 0.5 mg/ml | 1031 | 286017 | 489468 | | 277 | 475 | |
| | BDMQ | 1 mg/ml | | | | | | | |
| 37. | Avitex DN | 5 mg/ml | 372 | 33046 | 67404 | | 59 | 181 | |
| 38. | Avitex DN | 0.1 mg/ml | 687 | 251317 | 418395 | | 366 | 609 | |
| | BDMQ | 1 mg/ml | | | | | | | |
| 39. | Avitex E | 0.5 mg/ml | 674 | 273361 | 442352 | | 406 | 656 | |
| | BDMQ | 1 mg/ml | | | | | | | |
| 40. | DMQ-TEQ | 5 mg/ml | 826 | 198197 | 445457 | | 240 | 539 | |
| 41. | TBQ/THQ (35 mole % THQ) | 1 mg/ml | 20254 | 2910352 | 6446798 | | 144 | 318 | |
| | BDMQ | 1 mg/ml | | | | | | | |
| 42. | DMQ-TEQ | 5 mg/ml | 706 | 226048 | 502481 | | 320 | 712 | |
| | BDMQ | 1 mg/ml | | | | | | | |
| 43. | TBQ/THQ (35 mole % THQ) | 1 mg/ml | 20339 | 2415719 | 5398310 | | 119 | 265 | |
| | TBQ | 1 mg/ml | | | | | | | |
| 44. | DMQ-TEQ | 1 mg/ml | 893 | 370453 | 735995 | | 415 | 824 | |
| | TBQ | 1 mg/ml | | | | | | | |
| 45. | Zelec DP | 2.5 μl/ml | 1916 | 340564 | 8009917 | | 178 | 423 | |
| | phenyl-glucoside | 1 mg/ml | | | | | | | |
| | BDMQ | 1 mg/ml | | | | | | | |
| 46. | Zelec DP | 2.5 μl/ml | 2244 | 386368 | 1068947 | | 172 | 476 | |
| | phenyl-glucoside | 1 mg/ml | | | | | | | |
| | TBQ | 1 mg/ml | | | | | | | |

TABLE 7-continued

| | | | AMPPD | | | | | |
| | | | | Signal | | | S/N | |
| Additive | Concentration | Noise | 10 min | 30 min | 60 min | 10 min | 30 min | 60 min |
| 47. PVA<br>BDMQ | 1 mg/ml<br>1 mg/ml | 365 | 395636 | 476147 | | 1084 | 1305 | |

Applicants have endeavored to illustrate their invention by extensive embodiment of possible combinations. Nonetheless, it is recognized that the possible combinations are endless, and cannot be exhaustively embodied. Given the above teaching, those of ordinary skill in the art will arrive at enhancement agents and additives not specifically exemplified in the foregoing application. The examples are not intended to be limiting, and the identification of other combinations, given the foregoing disclosure, is well within the skill of those practicing this technology without undue experimentation. Such combinations are intended to be within the scope of the invention, save as expressly limited or excluded by the claims set forth below.

We claim:

1. A method for providing enhancement of luminescent intensity from a luminescent system, comprising:
    (1) contacting a 1,2-dioxetane compound with an effective amount of a luminescence enhancer compound comprising a polyonium salt and with an effective amount of a detergent;
    (2) inducing said 1,2-dioxetane to chemiluminesce and measuring the enhanced light intensity emitted from the system.

2. The method of claim 1, wherein said contacting is conducted in a liquid solution.

3. The method of claim 2, wherein said liquid solution is an aqueous solution.

4. The method of claim 1, wherein said dioxetane is induced to chemiluminesce by contacting said dioxetane with an activating agent.

5. The method of claim 4, wherein said dioxetane is protected by an enzyme-cleavable protective group, and said dioxetane is induced to chemiluminesce by contacting said dioxetane with an enzyme which removes said enzyme-cleavable group.

6. The method of claim 5, wherein said 1,2-dioxetane is of the formula

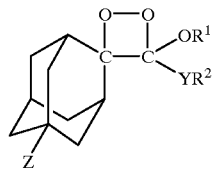

wherein $R^1$ is $C_1-C_{20}$ alkyl, $C_1-C_{12}$ aryl or aralkyl;
Y is phenyl or naphthyl;
$R^2$ is meta-substituted or non-conjugated on Y with respect to the dioxetane, is OX, wherein X is an enzyme cleavable group which, when cleaved, leaves the dioxetane phenoxy or naphthoxy anion and Z is H, Cl, other halogens, or a $C_{1-6}$ alkoxy group.

7. The method of claim 1, wherein said detergent is a surfactant selected from the group consisting of cationic, anionic, zwitterionic, non-ionic surfactants and mixtures thereof.

8. A method of determining the presence or amount an analyte substance in a test sample, comprising adding to said sample a 1,2-dioxetane which is caused to chemiluminesce by contact with an active agent, a salt and a detergent,
    simultaneous with the addition of said dioxetane to said sample or thereafter, adding said active agent, and
    determining the amount of chemiluminescence emitted, wherein the amount of chemiluminescence emitted is indicative of the presence and amount of analyte in said test sample, and is greater than the amount of chemiluminescence emitted in the absence of said polyonium salt and said detergent.

9. A method for enhancing the chemiluminescence from a molecule that is capable of being activated to generate a chemiluminescent signal which comprises:
    (a) providing a molecule that is capable of being activated to generate a chemiluminescent signal, wherein said molecule is a 1,2-dioxetane which is caused by an enzyme to decompose into a decomposition product which chemiluminescences, a polycationic surfactant, which polycationic surfactant is a water-soluble polyonium salt which, when added to said 1-2-dioxetane, results in the generation of greater chemiluminescence due to the composition of said 1,2-dioxetane than in the absence of said water-soluble polyonium salt, and a hydrophobic anionic enhancer which is selected from the group consisting of sodium dodecylbenzenesulfonate, sodium benzyl sulphate, sodium dodecyl sulphate, and mixtures thereof and
    (b) activating said dioxetane by causing it to decompose to generate a chemiluminescent signal.

10. The method of claim 9, wherein said 1,2-dioxetane has the formula:

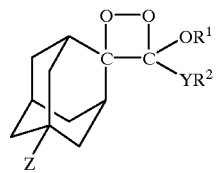

Z=H, Cl, other halogens or alkoxy groups;
$R^1$ is $C_1-C_{20}$ alkyl or $C_{1-2}$ aryl or aralkyl;
Y is phenyl or naphthyl;
$R^2$ is meta-substituted or nonconjugated on Y with respect to the dioxetane, and is OX, wherein;
X is an enzyme cleavable group which, when cleaved, leaves a dioxetane phenoxy or naphthoxy anion.

11. The method of claim 9, wherein said polycationic surfactant is a poly(vinylbenzyl quaternary ammonium salt).

12. The method of claim 11, wherein said poly (vinylbenzyl quaternary ammonium salt) is selected from the group consisting of poly(vinylbenzyltributyl ammonium chloride)(TBQ), poly(vinylbenzyldimethylbenzyl ammonium chloride) (BDMQ), and mixtures thereof.

13. The method of claim 9, further comprising the addition of an enhancement additive selected from the group consisting of benzyldimethyldodecyl ammonium bromide (BDMDAB), benzyldimethyltetradecyl ammonium chloride (BDMTDAC), and mixtures thereof.

14. A composition comprising a molecule that is capable of being activated to generate a chemiluminescent signal which is (a) 1,2-dioxetane that can be triggered to decompose and chemiluminesce; (b) a polycationic surfactant which is a polyonium salt, and a hydrophobic anionic enhancer selected from the group consisting of sodium benzyl sulphate, sodium dodecyl sulphate, sodium dodezylbenzensulfonate and mixtures thereof.

15. The composition of claim 13, wherein said 1,2-dioxetane has the formula:

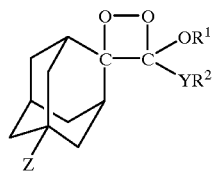

$Z$=H, Cl, other halogens or alkoxy groups;

$R^1$ is $C_1$–$C_{20}$ alkyl or $C_{1-12}$ aryl or aralkyl;

Y is phenyl or naphthyl;

$R^2$ is meta-substituted or nonconjugated on Y with respect to the dioxetane, and is OX, wherein;

X is an enzyme cleavable group which, when cleaved, leaves a dioxetane phenoxy or naphthoxy anion.

16. The composition of claim 14, wherein said polycationic surfactant is selected from the group consisting of TBQ, BDMQ, and mixtures thereof.

17. The method of claim 16, further comprising the addition of an enhancement additive selected from the group consisting of benzyldimethyldodecyl ammonium bromide (BDMDAB), benzyldimethyltetradecyl ammonium chloride (BDMTDAC), and mixtures thereof.

* * * * *